United States Patent [19]
Hopper et al.

[11] Patent Number: 6,005,000
[45] Date of Patent: Dec. 21, 1999

[54] 5,5-DISUBSTITUTED-3, 4-DIHYDROXY-2(5H)-FURANONES AND METHODS OF USE THEREFOR

[75] Inventors: Allen T. Hopper, Somerset, N.J.; John A. Ziemniak, Gwynedd Valley; Robert E. Johnson, Collegeville, both of Pa.

[73] Assignee: Oxis International, Inc., Portland, Oreg.

[21] Appl. No.: 08/915,099

[22] Filed: Aug. 20, 1997

Related U.S. Application Data

[60] Provisional application No. 60/024,440, Aug. 22, 1996, and provisional application No. 60/024,586, Aug. 26, 1996.

[51] Int. Cl.$^6$ .................. C07D 307/62; A61K 31/375
[52] U.S. Cl. .............................. 514/473; 549/315
[58] Field of Search ................ 549/315; 514/473

[56] References Cited

U.S. PATENT DOCUMENTS

| | | | |
|---|---|---|---|
| 5,071,872 | 12/1991 | Witiak et al. | 514/465 |
| 5,095,126 | 3/1992 | Witiak et al. | 549/315 |
| 5,185,366 | 2/1993 | Witiak et al. | 514/456 |
| 5,288,751 | 2/1994 | Brooks et al. | 514/438 |
| 5,298,526 | 3/1994 | Witiak et al. | 514/473 |
| 5,399,721 | 3/1995 | Hopper et al. | 549/315 |
| 5,504,107 | 4/1996 | Mantri et al. | 549/315 |
| 5,504,108 | 4/1996 | Witiak et al. | 514/473 |
| 5,534,540 | 7/1996 | Ulrich et al. | 514/473 |

FOREIGN PATENT DOCUMENTS

| | | |
|---|---|---|
| 4-29985 | 1/1992 | Japan . |
| WO 95/32194 | 11/1995 | WIPO . |

OTHER PUBLICATIONS

Alami et al, 1993, Tetrahedron Lett 34:6403–6.
Berson and Greenbaum, 1958, J Am Chem Soc 80:653–6.
Bisby et al, 1995, Free Rad Biol Med 20:411–20.
Boopathy and Baiasubramanian, 1968, Biochem J 239:371–7.
Brown, 1975, Organic Syntheses via Boranes, John Wiley and Sons, New York, 100, 178.
Buckle and Fenwick, 1989, J Chem Soc Perken Trans 1:477–82.
Buffinton and Doe, 1995, Free Rad Biol Med 19:911–8.
Bundy et al, 1995, J Med Chem 38:4161–3.
Coyle et al, 1993, Science 262:689–95.
DeJarlais et al, 1980, Synth Commun 10:653–60.
Egan and Gale, 1985, J Biol Chem 260;11554–9.
Evans et al, 1987, Biochem Pharm 36:2035–7.
Frimer et al, 1995, J Org Chem 60:4510–20.
Grisar et al, 1995, J Med Chem 38:453–8.
Gross et al, 1994, Hepato–Gastroenterol 41:320–7.
Halliwell, 1987, FASEB J 1:358–64.
Halliwell, 1991, Drugs 42:569–605.
Hopper et al. (1995) J. Org. Chem. 60:3334–41.
Hvoslef and Pedersen, 1979, Acta Chemica Scand B 33:503–11.
Kato et al, 1988, J Med Chem 31:793–8.
Kerwin, 1995, J Med Chem 38:4343–62.
King and Burns, 1975, the Second conference on Vitamin C, the New York Acadeny of Science, New York.
Lafont et al, 1995, J Clin Invest 95:1018–25.
Mansuy et al, 1996, Biochem Biophys Res Comm 135:1015–21.
Mantri and Witiak, 1994, Curr Med Chem 1:328–55.
Marshall et al, 1986, J Org Chem 51:858–63.
Maxwell, 1995, Drugs 49:345–61.
Millar et al, 1996, J Org Chem 51:4726–8.
Nicolaou and Webber, 1984, J. Chem Soc, Chem Commun 350–1.
Nihro et al, 1992, J Med Chem 35:1618–23.
Nunes et al, 1995, Thromb Vasc Biol 15:156–65.
Ochiai et al, 1991,J Am Chem Soc 113:1319–23.
O'Sullivan et al, 1992, Biochem Biophys Res Comm 187:1123–7.
Rabinovici et al, 1993, J Appl Physiol 74:1791–802.
Remacle et al, 1995, Mutat Res 316:103–22.
Saeva et al, 1991, J Am Chem Soc 113:5333–7.
Schank, 1972, Synthesis 176–90.
Schreck et al, 1992, Free Rad Res Comms 17:221–37.
Shimuzu et al, 1984, Pro Natl Acad Sci USA 81:689–93.
Silverman, 1992, The Organic Chemistry of Drug Design and Drug Action, Academic Press, San Diego, CA, 19–20.
Steinberg, 1995, Lancet 346:36–8.
Stork and Rychnovsky, 1987, J Am Chem Soc 109:1564–5.
Sun, 1990, Free Rad Biol & Med 8:583–99.
Triozzi et al, 1993, Int J Immunopharmac 15:47–54.
Wang et al, 1996, Pharm Exp Therap 277:714–20.
Wimalasena et al, 1994, Biochem Biophys Res Comm 200:113–9.
Witiak et al, 1982, J Med Chem 25:90–3.
Witiak et al, 1986, J Med Chem 29:2170–4.
Witiak et al, 1987, J Org Chem 52:2324–7.
Witiak et al, 1987, Actual Chim Therap 15:41–62.
Witiak et al, 1988, J Med Chem 31:1437–45.
Witiak et al, 1992, in Trends in Medicinal chemistry '90, Proceeding of the XIth International Symposiumon Medicinal Chemistry, Jerusalem, Israel, Sep. 2–7, Sarel et al eds. Blackwell Scientific Publicstions, Oxford, London :243–56.

*Primary Examiner*—Bernard Dentz
*Attorney, Agent, or Firm*—Klauber & Jackson

[57] ABSTRACT

The present invention relates to synthetic methods for the production of both optically active and racemic 5,5-disubstituted-3,4-dihydroxy-2(5H)-furanones; 5-[(4-aryl)-3-butynyl]-3,4-dihydroxy-2(5H)-furanones; 5-(2-arylthio) ethyl-3,4-dihydroxy-2(5H)-furanones; and 5-(2-aryloxy) ethyl-3,4-dihydroxy-2(5H)-furanones. This invention further relates to the use of the above mentioned compounds as anti-inflammatory agents through their action as mixed inhibitors of lipid peroxidation, 5-lipoxygenase, cyclooxygenase-1 and cyclooxygenase-2. The invention further relates to the use of such compounds in the treatment of chronic inflammatory disorders such as asthma, rheumatoid arthritis, inflammatory bowel disease, atherosclerosis, acute respiratory distress syndrome, and central nervous system disorders such as Alzheimer's and Parkinson's disease wherein reactive oxygen species and inflammatory mediators are contributing deleterious factors.

15 Claims, No Drawings

5,5-DISUBSTITUTED-3, 4-DIHYDROXY-2(5H)-FURANONES AND METHODS OF USE THEREFOR

This application claims priority from Provisional applications Ser. Nos. 60/024,440 filed on Aug. 22, 1996, and 60/024,586 filed Aug. 26, 1996.

FIELD OF THE INVENTION

The present invention relates generally to 5-substituted and 5,5-disubstituted-3,4-dihydroxy-2(5H)-furanones, methods of preparation therefor, and methods for their use.

BACKGROUND OF THE INVENTION

The aci-reductone 4-(4-chlorophenyl)-2-hydroxytetronic acid compound (CHTA) possesses antilipidemic and anti-aggregatory properties which differ from those of the classical phenoxyactetic acids as has been disclosed in Witiak et al., *J. Med. Chem.*, 1988, 31:1434–1445 and Kamanna et al., *Lipids*, 1989, 24:25–32. Although unsubstituted-, 2-alkyl- and 2-acyltetronic acids are frequently found in nature, the 2-hydroxy substituted tetronic acid redox system is found only in vitamin C and its closely related relatives (isoascorbic acid, erythroascorbic acid) and derivatives, and the macrolide antibiotic, chlorothricin.

The antiaggregatory activities of 2-hydroxytetronic acid aci-reductone compound (CHTA) are of interest since blood platelets are involved in the genesis of atherosclerosis. 2-Hydroxytetronic acid aci-reductones inhibit collagen-induced human platelet aggregation and secretion of [$^{14}$C]-serotonin in a concentration-dependent manner at equivalent doses, as reported in Witiak et al., *J. Med. Chem.*, 1982, 25:90–93. The CHTA compound inhibits platelet function by a similar mechanism, involving arachidonic acid release. Redox analogues, such as 2-hydroxytetronic acid, function as antioxidants in membranes or interfere with free radical processes involved in the biosynthetic elaboration of cyclic prostaglandin endoperoxides ($PGG_2$ and $PGH_2$), and, subsequently, thromboxane $A_2$ from arachidonic acid.

The development of dual antioxidant-arachidonic acid (AA) metabolism inhibitors may provide added benefits over existing drugs for the treatment of diseases associated with oxidative stress and inflammation. Numerous conditions including asthma, rheumatoid arthritis, irritable bowel disease (IBD), adult respiratory distress syndrome (ARDS), atherosclerosis, ischemia/reperfusion injury, restenosis, neurodegenerative disorders and initiation and promotion of carcinogenesis correlate with abnormally high levels of reactive oxygen species (ROS). Antioxidant- based therapies including both natural antioxidants (e.g., vitamin E, vitamin C and SOD), and synthetic antioxidants (e.g., 4-aryl-2-hydroxytetronic acids[1], 2-O-alkyl ascorbic acids, probucol and tirilazad mesylate) have been, or are currently being, investigated for the treatment of a number of these conditions.

Previously, the S-arachidonic acid aci-reductone analog (S)-3,4-dihydroxy-5[(all Z)-3,6,9,12-octadecatraenyl]-2(5H)-furanone, was identified as a stereoselective and potent arachidonic acid metabolic inhibitor. This compound inhibits both $PGE_2$ and $LTB_4$ production in stimulated macrophages ($IC_{50}$=20 μM) and blocks AA-induced platelet aggregation (AAIPA) with an $IC_{50}$<10 μM. Dual cyclooxygenase (COX) and lipoxygenase (LO) activity could be important in preventing substrate shunting in the arachidonic acid cascade. Although this compound demonstrates an encouraging biological profile, both its instability and labored synthesis render this compound less than satisfactory as a therapeutic agent.

Thus, there exists a need for new therapeutic agents which exhibit activity as antioxidants and arachidonic acid metabolism inhibitors. It is to this aim that the present invention is directed.

SUMMARY OF THE INVENTION

The present invention relates to 5-substituted and 5,5-disubstituted-3,4-dihydroxy-2(5H)-furanones of the general formula I

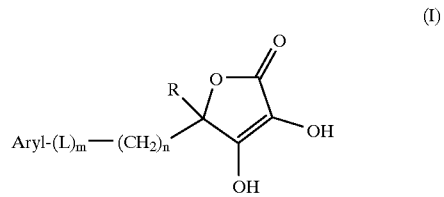

(I)

wherein R is hydrogen, phenyl or lower alkyl; L is a linker moiety selected from the group consisting of oxygen, sulfur, nitrogen, acetylene, a cis or trans carbon-carbon double bond, an ester, carbonate, urea, amide and carbamate; m is 0 or 1; n is 0 to 4; Aryl is a substituted or unsubstituted aryl group; with the proviso that when R is hydrogen, then either m or n is not zero, and the pharmaceutically acceptable salts thereof.

In various preferred embodiments of the present invention, these compounds are represented by four structural subclasses of compounds. Thus, in one preferred embodiment, the compounds are 5,5-disubstituted-3,4-dihydroxy-2(5H)-furanones of the structural formula Ia

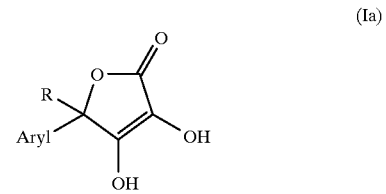

(Ia)

wherein R and Aryl are as hereinbefore defined. Most preferably, in the compounds of formula (Ia), R is a methyl, 1-propyl or 2-methylpropyl group; and Aryl is a phenyl, or substituted phenyl, such as 1,1$^1$-biphenyl, 4-chlorophenyl or 2-methylpropylphenyl group.

In a second preferred embodiment, the compounds are 5-(aryl alkynyl)-3,4-dihydroxy-2(5H)-furanones of the structural formula Ib

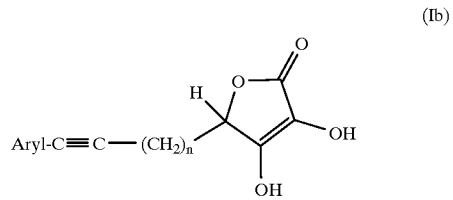

(Ib)

wherein n and Aryl are as hereinbefore defined. Most preferably, in the compounds of formula Ib, n is 2 and Aryl is naphthyl or a substituted phenyl such as 2-methylphenyl, 2-hexenyl phenyl, 2-phenylthiomethylphenyl or pentylthiomethyl phenyl.

In a third preferred embodiment, the compounds are 5-(arylthio)alkyl-3,4-dihydroxy-2(5H)-furanones of the structural formula Ic

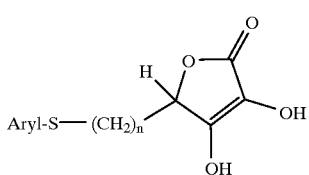

(Ic)

wherein n and Aryl are as hereinbefore defined. Most preferably, in the compounds of Formula Ic, n is 2 and the Aryl substituent is napthyl or 4,5-diphenylisoxazole.

In a fourth preferred embodiment, the compounds are 5-(aryloxy)alkyl-3,4-dihydroxy-2(5H)-furanones of the structural formula Id

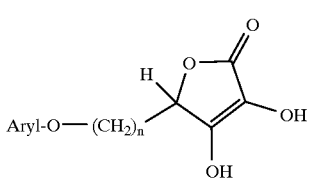

(Id)

wherein n and Aryl are as hereinbefore defined. Most preferably, in the compounds of formula Id, n is 2 and Aryl is a substituted phenyl or heteroaryl compound such as 1,1$^2$ biphenyl-4 yl, 4-phenoxyphenyl, flavonyl, dibenzofuranyl, quinolinyl and naphthyl.

The racemic 5,5-disubstituted analogs of formula Ia are prepared by reacting an ethyl benzoylformate with a Grignard reagent and trapping the intermediate alkoxide anion with benzyloxyacetyl chloride, and subsequently adding lithium diisopropylamide to generate the corresponding 3-benzyloxy-5,5-disubstituted-4-hydroxy-2(5H)-furanones. Cleavage of the benzyl group by hydrogenolysis provides racemic 5,5-disubstituted-3,4-dihydroxy-2(5H)-furanones of formula Ia.

The enantiomerically pure 5,5-disubstituted analogs of formula Ia are synthesized by reacting ethyl benzoylformate with a Grignard reagent, followed by ester saponification and resolution of the resultant 2-aryl-2-substituted-2-hydroxy acid by crystallizing with a suitable optically pure chiral amine to provide the optically pure compounds with non-racemisable stereocenters. Acid esterification, acylation of the hydroxyl group with benzyloxyacetyl chloride, LDA-induced intramolecular Claisen cyclization and reductive cleavage of the benzyl protecting group generates the 5,5-disubstituted-3,4-dihydroxy-2(5H)-furanones of formula Ia having high enantiomeric purity.

The 5-(aryl alkynyl)-3,4-dihydroxy-2(5H)-furanones of formula Ib are synthesized in a convergent manner by coupling 5-(alkynyl)-3,4-dihydroxy-2(5H)-furanone with aryliodides by employing a catalytic amount of Pd(PPh$_3$)$_4$. The starting material, 5-(alkynyl)-3,4-dihydroxy-2(5H)-furanone, is synthesized in four steps. For instance, intermolecular Claisen reaction between α-trimethylsilyloxy-γ-butyrolactone and ethyl benzyloxyacetate yields 3-benzyloxy-4-hydroxy-5-(2-hydroxyethyl)-2(5H)-furanone. Iodination (I$_2$, PPh$_3$, imidazole), subsequent iodo displacement with lithium acetylide, and benzyl group cleavage yields, for instance, the 5-(3-butynyl)-3,4-dihydroxy-2(5H)-furanone coupling precursor.

The 5-(arylthio)alkyl-3,4-dihydroxy-2(5H)-furanones of formula Ic are produced by reacting a 3,4-dihydroxy-5-(iodoalkyl)-2(5H)-furanone with the lithium salt of a substituted arylthiol. The starting material, 3,4-dihydroxy-5-(2-iodoalkyl)-2(5H)-furanone is produced by benzyl group cleavage of 3-benzyloxy-4-hydroxy-5-(2-iodoalkyl)-2(5H)-furanone.

The 5-(aryloxy)alkyl-3,4-dihydroxy-2(5H)-furanones of formula Id are prepared by coupling 3,4-dibenzyloxy-5-(hydroxyalkyl)-2(5H)-furanone with an appropriately substituted phenol according to the Mitsunoble reaction. Subsequent benzyl group cleavage by hydrogenation yields the desired 5-(aryloxy) alkyl-3,4-dihydroxy-2(5H)-furanone.

DETAILED DESCRIPTION OF THE INVENTION

As used herein, the term "alkenyl" means an organic, alkanyl group containing one or more double bonds and which can optionally be substituted by one or more halogen, lower alkanyl, alkoxy, aromatic or heteroaromatic groups. Examples of unsubstituted alkenyl groups include those such as 3-butenyl, 3- or 4-pentenyl, and the like. In a similar fashion, the term "alkynyl" refers to an organic, alkanyl group containing one or more triple bonds, of which 3-butynyl, 3- or 4- pentynyl and the like are representative.

The term "substituted or unsubstituted aryl", as utilized herein, means an organic, aromatic group which can be unsubstituted or substituted by one or more lower alkyl, lower alkenyl, lower alkenynyl, loweralkylthio, loweralkylsulfonyl, loweralkylsulfonylamino, aromatic or heteroaromatic groups. Examples of unsubstituted aryl groups include phenyl, pyridyl, thiophenyl, furyl, pyrrolyl and the like. Examples of substituted aryl groups include those such as alkyl-substituted aryl, e.g., tolyl, 3-methylpyridyl, 2,3-dimethylphenyl, 4-ethylphenyl, 4-isobutylphenyl; alkoxysubstituted aryl, e.g., 4-methoxyphenyl; loweralkylthio or loweralkylsulfonyl-substituted aryl, e.g., 1-propylthiophenyl, 1-pentylsulfonylphenyl, lower alkenyl substituted phenyl, e.g., 4-(2-(2Z-hexenyl]phenyl and aryl-substituted aryl, e.g., 1,1'-biphenyl and naphthyl. Complex aryl groups such as those derived from flavone, dibenzofuran, 1,8-natphthalimide, 1,8-naptholsultam, quinoline, 4,5-diphenyl-2-thio-1,3-isoxazole, and napthalenethiol can also be utilized as substituant groups. Particularly preferred are compounds wherein a 2- or 2,3-disubstitution pattern (relative to the alkenenyl or alkynenyl group) is present.

As used herein, the term lower "alkyl" means straight- or branched-chain saturated aliphatic hydrocarbon groups preferably containing 1–6 carbon atoms. Representative of such groups are methyl, ethyl, isopropyl, isobutyl, butyl, pentyl, hexyl and the like.

The term "alkoxy" means a lower alkyl group attached to the remainder of the molecule by oxygen. Examples of alkoxy include methoxy, ethoxy, propoxy, isopropoxy and the like.

The compounds of formula I can be formed as mixtures of enantiomers, as well as cis/trans isomers, due to the asymmetric carbon atoms of the ring structure and the double bonds present in the substituents. The present invention contemplates the use of both the individual isomers, as well as the racemic or cis/trans mixtures or both.

The present invention relates to 5-substituted-and 5,5-disubstituted-3,4-dihydroxy-2(5H)-furanones of the general formula,

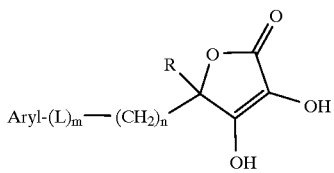

(I)

wherein R is hydrogen, phenyl, or a lower alkyl; L is a linker moiety selected from the group consisting of oxygen, sulfur, nitrogen, acetylene, a cis or trans carbon-carbon double bond, an ester, carbonate, urea, amide and carbamate; m is 0 or 1, n is 0 to 4, Aryl is a substituted or unsubstituted aryl group; with the proviso that when R is hydrogen, then either m or n is not zero; and the pharmaceutically acceptable salts thereof.

In general, the compounds of formula I wherein m and n are zero are prepared by:

a) reacting a benzoylformate of the formula,

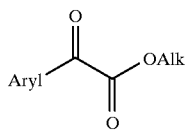

(II)

wherein Alk is a lower alkyl group, Aryl is as hereinbefore defined with an organometalic reagent RMX wherein M is a group I or group II metal, X is a halogen, and R is as hereinbefore defined, to form an intermediate alkoxide of the formula,

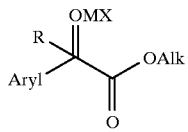

(III)

wherein Aryl, R, M, Alk and X are as hereinbefore defined. The intermediate alkoxide is treated with a benzyloxyacetyl chloride, wherein Bn is a protecting group such as benzyl or a substituted derivative thereof, to provide an intermediate diester of the formula,

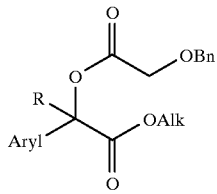

(IV)

wherein Aryl, R and Alk are as hereinbefore defined;

(b) Intramolecular Claisen cyclization of the diester of formula IV to the tetronic acid of the formula,

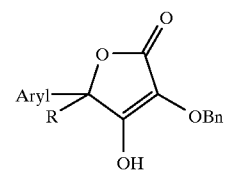

(V)

wherein Aryl, R and Bn are as hereinbefore defined; and (c) cleaving the benzyl protecting group of formula V by catalytic hydrogenation to yield the desired 5,5-disubstituted-3,4-dihydroxy-2(5H)-furanone of the general formula I wherein Aryl and R are as hereinbefore defined, and m and n are 0.

Step (a) of the instant process utilizes as starting material, the appropriate benzoyl formate of the formula II wherein Aryl and Alk are as hereinbefore defined which can be purchased through commercial suppliers, or, if not commercially available, synthesized according to literature procedures. Benzoylformates are prepared by mixing an aryl compound, alkyl oxalylchloride and AlCl$_3$ (or suitable Lewis acid) in a 1.0/1.1/1.1 mixture in 1,2-dichloroethane (or suitable solvent) at 0_ to 10_C with vigorous stirring and subsequently stirring the reaction mixture at 25_C for 24 hours according to the method of Kuchar et al., *Coll. Czech. Chem. Commun.*, 49: 122–136 (1984).

A process for the synthesis of enantiomerically pure analogs of the formula I wherein m and n are both zero comprises:

(a) reacting an optically pure 2-hydroxyester of the formula

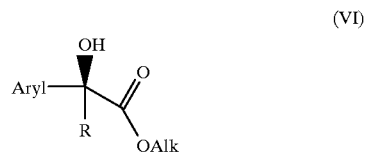

(VI)

wherein Aryl, R and Alk are as hereinbefore defined with a benzyloxyacetyl chloride, wherein Bn is as hereinbefore defined, to provide an intermediate diester of the formula,

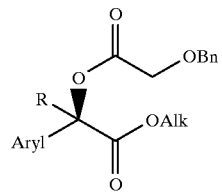

(VII)

wherein Aryl, R, Bn, Alk and R are as hereinbefore defined;

(b) Intramolecular Claisen cyclization of the diester of formula VII to the tetronic acid of the formula,

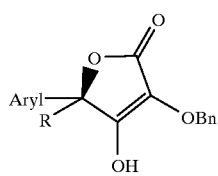

(VIII)

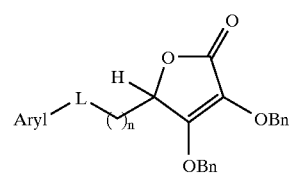

(XI)

wherein Aryl, R and Bn are as hereinbefore defined; and (c) cleaving the benzyl protecting group of formula VIII by catalytic hydrogenation to yield the desired optically pure 5,5-disubstituted-3,4-dihydroxy-2(5H)-furanone of the general formula I wherein Aryl and R are as hereinbefore defined, and m and n are both zero.

Step (a) of this process utilizes as starting material, an optically pure 2-hydroxyester of the formula VI, wherein Aryl, R and Alk are as hereinbefore defined, which can be purchased through commercial suppliers or, if not commercially available, synthesized according to literature procedures. Reaction of a benzoylformate with an organometalic reagent RMX, wherein R, M, and X are as hereinbefore defined, produces racemic 2-hydroxyesters of the formula VI, wherein aryl, R and Alk are as hereinbefore defined. Ester saponification with, for example, 1.0 M NaOH, resolution with an optically pure amine base using the method of Saigo et al., *Bull. Chem. Soc. Jpn.*, 55: 1188–1190 (1982) and esterification of the acid with, for example an etheral solution of $CH_2N_2$, provides optically pure 2-hydroxyesters of the formula VI.

A process for the synthesis of analogs of formula I wherein R is hydrogen, Aryl is as hereinbefore defined, m is 1 n=2, and L is an oxygen, ester, N-sulfonamide or N-imide linkage comprises:

(a) reacting a 3-benzyloxy-4-hydroxy-5-(2-hydroxyethyl)-2(5H)-furanone of the formula,

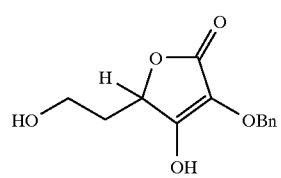

(IX)

wherein Bn is as hereinbefore defined with one equivalent of BnBr and one equivalent of triethlyamine in THF for 5 hours at 65_C to provide 3,4-dibenzyloxy-5-(2-hydroxyethyl)-2 (5H)-furanone of the formula,

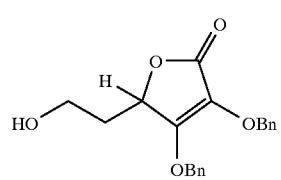

(X)

wherein Bn is as hereinbefore defined;

(b) reacting the 3,4-dibenzyloxy-2(5H)-furanone of the formula X with an aryl alcohol (i.e. phenol), carboxylic acid, sulfonamide, or phthalimide, wherein aryl is as hereinbefore defined, under Mitsunoble conditions to provide 3,4-dibenzyloxy-2(5H)-furanones of the formula, wherein Aryl and Bn are as hereinbefore defined, L is an oxygen, ester, N-sulfonamide or N-imide linkage and n=2; and (c) cleaving the benzyl protecting groups of formula XI by catalytic hydrogenation to yield the desired 5-substituted-3,4-dihydroxy-2(5H)-furanone of the general formula I wherein R is hydrogen, Aryl is as hereinbefore defined, m is 1, n=2, and L is an oxygen, ester, N-sulfonamide or N-imide linkage.

A process for the synthesis of analogs of the formula I wherein R is hydrogen, Aryl is as hereinbefore defined, m is 1, n=2, and L is a sulfur linkage comprises:

(a) Iododination of the 3-benzyloxy-4-hydroxy-5-(2-hydroxyethyl)-2(5H)-furanone of the formula IX with $I_2$, $PPh_3$ and imidazole in $CH_3CN$/ether (1/5) to produce the 3-benzyloxy-4-hydroxy-5-(2-iodoethyl)-2-(5H)-furanone of formula,

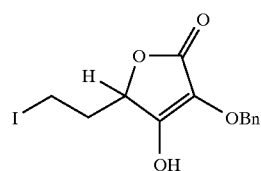

(XII)

wherein Bn is as hereinbefore defined;

(b) benzyl group cleavage by first treating the furanone of formula XII with acetyl anhydride and pyridine in $CH_2Cl_2$ for 2 hours, followed by removal of all volatile substances in vacuo and subsequent treatment with boron trichloride to yield 3,4-dihydroxy-5-(2-iodoethyl)-2(5H)-furanone of the formula;

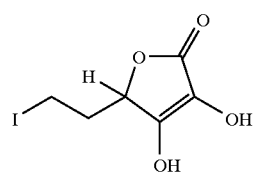

(XIII)

(c) reaction of a compound with the formula XIII with three mole equivalents of the lithium salt of an arylthiol, wherein aryl is as hereinbefore defined, provides compounds of the formula I wherein Aryl is as hereinbefore defined, n=2, R=H, and L is sulfur.

A process for the synthesis of analogs of the formula I wherein R is hydrogen, Aryl is as hereinbefore defined, m is 1, n=2, and L is an acetylene or carbon-carbon double bond linkage comprises:

(a) reaction of 5-(2-iodoethyl)-2-(5H)-furanone of the formula XII with lithium acetylide ethylenediamine complex in HMPA at –5_C to make 3-benzyloxy-4-hydroxy-5-(3-butynyl)-2-(5H)-furanone of formula,

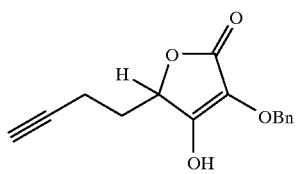

(XIV)

wherein Bn is as hereinbefore defined;

(b) benzyl group cleavage by first treating the furanone of formula XIV with acetyl anhydride and pyridine in $CH_2Cl_2$ for 2 hours, followed by removal of all volatile substances in vacuo and subsequent treatment of the remaining residue with boron trichloride to yield compounds of the general formula;

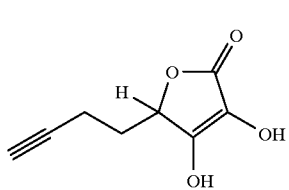

(XV)

(c) coupling the 5-(3-butynyl)-2(5H)-furanone of formula XV with an aryliodide to provide analogs of the formula I, wherein Aryl is as hereinbefore defined, n=2, R=H and L is an acetylene linker;

(d) reduction of the acetylene moiety by the addition of 1 mole equivalent of $H_2$ by catalytic hydrogenation under Lindlar conditions to yield compounds of formula I wherein Aryl is as hereinbefore defined, n=2, R=H and L is a carbon-carbon cis double bond; and (e) reduction of the acetylene moiety by the addition of 2 mole equivalent of $H_2$ by catalytic hydrogenation to yield compounds of formula I wherein Aryl is as hereinbefore defined, m=0, n=4, and R is hydrogen.

In a composition aspect, the present invention encompasses novel pharmaceutical compositions comprising the compounds of the general formula I, together with a physiologically acceptable carrier or excipient, in an amount sufficient to have antilipidemic, antiaggregatory or antiinflammatory activities in an animal or patient. The compounds and their compositions of the present invention are thus useful in the treatment or prevention of atherosclerotic disorders, as well as in the treatment of various pathologies in which acute and chronic inflammation occur.

The starting materials utilized in the synthesis of the compounds of formula I are known in the art and/or are preparable by methods described herein. Where the pure optical isomers of these compounds are desired, numerous methods exist for the manufacture of optically active and optically pure derivatives of the necessary starting materials. Also, a wide range of chiral bases can be used to starting materials and intermediate products. Partial separation of enantiomers can typically accomplished with optically active solvents such as (−)-menthone, (−)-menthyl acetate and (+)-limonene. Anion-exchange chromatography using a chiral stationary phase constructed of 1-p-nitrophenyl-2-amino-1,3-propanediol, or chromatography through starch successfully separates mandelic acid enantiomers.

The invention also provides for pharmaceutical compositions comprising the compounds of formula I above, as well as their physiologically acceptable salts (such as, for example, $Na^+$, $K^+$, $NH_4^+$).

The compounds of the invention have antilipidemic and antiaggregatory activity and are thus useful in the treatment or prevention of atherosclerotic disorders. Additionally, the compounds of the invention possess the ability to inhibit the activity of cyclooxygenase and 5-lipooxygenase in standardized assays for such activity, thus making them useful for the treatment of pathologies involving acute or chronic inflammation, such as inflammatory bowel disease, asthma, adult respiratory distress syndrome (ARDS) and various forms of arthritis.

BIOLOGICAL EVALUATION

The compounds of the invention were screened for their anti-inflammatory activity using a series of in vitro tests the details of which are given below. The activity of various compounds against 5-lipoxygenase, cycloxygenase-1, cycloxygenase-2 and lipid peroxidase was evaluated. Results of the screening procedures are included in TABLE I, and the activity against 5-lipoxygenase at a test concentration of 1 $\mu$M in Table II.

5-LIPOXYGENASE SCREEN

5-Lipoxygenase catalyzes the oxidative metabolism of arachidonic acid to 5-hydroperoxyeicosatetraenoic acid (5-HETE), the initial reaction leading to the formation of the leukotrienes. Briefly, the testing procedure utilizes a crude enzyme preparation from rat basophilic leukemia cells (RBL-1) according to the methods of T. Shimuzu et al. *Pro. Natl. Acad, Sci.* 81:689–693 (1984) and R. W. Egan et al, *J. Biol. Chem.* 260: 11554–11559 (1985). Test compounds are pre-incubated with the enzyme preparation for 5 minutes at room temperature and the reaction is initiated by the addition of arachidonic acid. Following an 8 minute incubation at room temperature, the reaction is terminated by the addition of citric acid and concentrations of 5-HETE are determined by RIA. Compounds are screened at 30 $\mu$M. Under these conditions the reference compound phenidone has an $IC_{50}$ of 30 $\mu$M.

CYCLOOXYGENASE-1 SCREEN

Cyclooxygenase-1 is involved in the formation of prostaglandins and thromboxane via the oxidative metabolism of arachidonic acid. Briefly, cyclooxygenase from ram seminal vesicles is incubated with arachidonic acid (100 $\mu$m) for 2 minutes at 37° C. in the presence or absence of test compounds according to the methods of A. T. Evans et al., *Biochem. Pharm.* 36:2035–2037 (1987) and R. Boopathy et al., *Biochem J.* 239:371–377 (1968). The assay is terminated by the addition of trichloroacetic acid and cyclooxygenase activity is determined by reading the absorbance at 530 nm. Compounds are screened at 300 $\mu$M. Under these condition the reference compound aspirin has an $IC_{50}$ value of 240 $\mu$M.

CYCLOOXYGENASE-2 SCREEN

Cyclooxygenase-2, also known as prostaglandin H synthetase-2, catalyzes the rate-limiting step in the synthesis of inflammatory prostaglandins. In this reaction cyclooxygenase-2 catalyzes the oxygenation of unesterified precursors to form cyclic endoperoxide derivatives, including prostaglandin H. Briefly, cyclooxygenase-2 from sheep placenta, 14 $\mu$g/assay tube, is incubated with arachidonic acid (500 $\mu$M) for 1.5 minutes at 27° C. in the absence or presence of test compounds according to the methods of A. T. Evans, et al., *Biochem Pharm.* 36:2035–2037 (1987) and M. G. O'Sullivan et al., *Biochem. Biophys. Res. Cxomm.* 187:1123–1127 (1992). The assay is terminated by the addition of trichloroacetic acid and cyclooxygenase activity is determined by reading the absorbance at 532 nm. Compounds are screened at 300 $\mu$M. Under these conditions the reference compound NS-398 exhibited 77% inhibition at 300 $\mu$M.

LIPID PEROXIDATION SCREEN

Lipid peroxidation is a consequence of various stimuli, including reactive free radicals. Polyunsaturated fatty acids associated with plasma membranes are degraded due to enzymatic induction by reactive agents such as $CCl_4$, leading to cellular damage. Briefly, microsomes are prepared from rat livers and the protein concentration is determined according to the method of D. Mansuy et al., *Biochem. Biophys. Res. Comm.* 135:1015–1021 (1986). A reaction mixture consisting of 2 mg of the microsomal preparation, an NADPH generating system, 20 mM $CCl_4$ and test compound are incubated for 12 minutes at 37° C. The reaction is terminated by the addition of a mixture of thiobarbituric acid and trichloroacetic acid. The absorbance is read at 535 nm and is proportional to the concentration of malondialdehyde. Compounds are screened at 300 $\mu$M. Under these conditions the reference compound, alpha-tocopherol has an $IC_{50}$ value of 280 $\mu$M.

TABLE I

| Example # | Compound Name | (PERCENT INHIBITION) | | | |
|---|---|---|---|---|---|
| | | COX-1 (300 $\mu$M) | COX-2 (300 $\mu$M) | 5-LO (30 $\mu$M) | LPO (300 $\mu$M) |
| 1 | 3,4-Dihydroxy-5-methyl-5-phenyl-2(5H)-furanone | −12 | 3 | 58 | 63 |
| 2 | 5-[(1,1'-Biphenyl)-4-yl]-3,4-dihydroxy-5-methyl-2(5H)-furanone | 33 | 22 | 107 | 78 |
| 3 | 3,4-Dihydroxy-5-methyl-5-[4-(2-methylpropyl)phenyl]-2(5H)-furanone | 2 | −4 | 99 | 78 |
| 4 | 5-(4-Chlorophenyl)-3,4-dihydroxy-5-methyl-2(5H)-furanone | 2 | 24 | 2 | 54 |
| 5 | 5-[(1,1'-Biphenyl)-4-yl]-3,4-dihydroxy-5-propyl-2(5H)-furanone | 13 | 22 | 99 | 70 |
| 6 | 5-[(1,1'-Biphenyl)-4-yl]-3,4-dihydroxy-5-(2-methylpropyl)-2(5H)-furanone | 67 | 46 | 96 | 82 |
| 7 | 5-[(1,1'-Biphenyl)-4-yl]-3,4-dihydroxy-5-phenyl-2(5H)-furanone | 52 | 34 | 102 | 73 |
| 8 | 3,4-Dihydroxy-5,5-diphenyl-2(5H)-furanone | 15 | 17 | 94 | 70 |
| 9 | 3,4-Dihydroxy-5-(4-isobutylphenyl)-5-(1-propyl)-2(5H)-furanone | 25 | 19 | 82 | 79 |
| 10 | 3,4-Dihydroxy-5-(4-isobutylphenyl)-5-phenyl-2(5H)-furanone | 43 | 34 | 106 | 89 |
| 11 | (S)-(+)-5-[(1,1'-Biphenyl)-4-yl]-3,4-dihydroxy-5-methyl-2(5H)-furanone | 34 | 10 | 101 | 71 |
| 12 | (R)-(−)-5-[(1,1'-Biphenyl)-4-yl]-3,4-dihydroxy-5-methyl-2(5H)-furanone | 10 | 12 | 101 | 62 |
| 13 | (R)-(−)-3,4-Dihydroxy-5-methyl-5-[4-(2-methylpropyl)phenyl]-2(5H)-furanone | 12 | 14 | 102 | 76 |
| 14 | (S)-(+)-3,4-Dihydroxy-5-methyl-5-[4-(2-methylpropyl)phenyl]-2(5H)-furanone | 12 | 18 | 96 | 66 |
| 15 | 3,4-Dihydroxy-5-[2-(4-phenoxy)phenoxyethyl]-2(5H)-furanone | 9 | −4 | 100 | −5 |
| 16 | 3,4-Dihydroxy-5-[2-(flavone-6-oxy)ethyl]-2(5H)-furanone | 17 | 2 | 100 | 76 |
| 17 | 5-[2-(Dibenzofuran-2-oxy)ethyl]-3,4-dihydroxy-2(5H)-furanone | 17 | 21 | 99 | 74 |
| 18 | 3,4-Dihydroxy-5-[2-(1-naphthoxy)ethyl]-2(5H)-furanone | 11 | −12 | 99 | 71 |
| 19 | 3,4-Dihydroxy-5-[2-(1,8-naphthalimide)-N-ethyl]-2(5H)-furanone | 9 | 2 | 86 | 68 |
| 20 | 3,4-Dihydroxy-5-[2-(1,8-naphthosultam)-N-ethyl]-2(5H)-furanone | −15 | 13 | 91 | 61 |
| 21 | 3,4-Dihydroxy-5-[2-(diphenylmethane-2-oxy)ethyl]-2(5H)-furanone | 12 | 10 | 101 | 68 |
| 22 | 5-[2-((1,1'-Biphenyl)-4-oxy)ethyl]-3,4-dihydroxy-2(5H)-furanone | 18 | 10 | 99 | 74 |
| 23 | 3,4-Dihydroxy-5-[2-(quinoline-2-oxy)ethyl]-2(5H)-furanone | 8 | −2 | 93 | 69 |
| 24 | 3,4-Dihydroxy-5-[2-(4,5-diphenyl-1,3-isoxazole-2-thio)ethyl]-2(5H)-furanone | 76 | 68 | 113 | 78 |
| 25 | 3,4-Dihydroxy-5-[2-(naphthyl-1-thio)ethyl]-2(5H)-furanone | 6 | 19 | 102 | 74 |
| 26 | 3,4-Dihydroxy-5-[2-(naphthyl-2-thio)ethyl]-2(5H)-furanone | 12 | 12 | 101 | 77 |
| 27 | 3,4-Dihydroxy-5-[(4-phenyl)-3-butynyl]-2(5H)-furanone | 5 | 20 | 42 | 59 |
| 28 | 3,4-Dihydroxy-5-[(4-(2-methyl)phenyl)-3-butynyl]-2(5H)-furanone | 4 | 15 | 58 | 61 |
| 29 | 3,4-Dihydroxy-5-[(4-(2-(2Z-hexenyl))phenyl)-3-butynyl]-2(5H)-furanone | 55 | 26 | 81 | 72 |
| 30 | 3,4-Dihydroxy-5-[(4-(2-(phenylthio)methyl)phenyl)-3-butynyl]-2(5H)-furanone | 26 | 16 | 100 | 62 |
| 31 | 3,4-Dihydroxy-5-[(4-(2-phenylsulfonamide-(N-butyl)-3-butynyl]-2(5H)-furanone | 7 | 23 | 81 | 73 |
| 32 | 3,4-Dihydroxy-5-[4-(2-naphthyl)-3-butynyl]-2(5H)-furanone | 34 | 23 | 98 | 75 |
| 33 | 3,4-Dihydroxy-5-[(4-(2-(propylthio)methyl)phenyl)-3-butynyl]-2(5H)-furanone | 37 | 20 | 84 | 74 |
| 34 | 3,4-Dihydroxy-5-[(4-(2-(1-pentylthio)methyl)phenyl)-3-butynyl]-2(5H)-furanone | 67 | 43 | 92 | 63 |
| 35 | 3,4-Dihydroxy-5-[(4-(2-(propylsulfonyl)methyl)phenyl)-3-butynyl]-2(5H)-furanone | 25 | 13 | 30 | 60 |
| 36 | 3,4-Dihydroxy-5-[2-(4-(4-fluorophenylmethyl)thiophene)-(3-butynyl)]-2(5H)-furanone | NT | NT | 85 @ 1 | NT |
| 37 | 3,4-Dihydroxy-5-[(4-phenylbutanyl)-2(5H)-furanone | NT | NT | NT | NT |
| 38 | 3,4-Dihydroxy-5-[(4-phenyl)-3Z-butenyl]-2(5H)-furanone | NT | NT | NT | NT |
| 39 | 3,4-Dihydroxy-5[(4-(2-methyl)phenyl)-3Z-butenyl]-2(5H)-furanone | NT | NT | NT | NT |
| 40 | 3,4-Dihydroxy-5[(4-(2-(2Z-hexenyl))phenyl)-3Z-butenyl]-2(5H)-furanone | 38 | 25 | 99 | 65 |

TABLE II

The effect of various aci-reductones on 5-Lipoxygenase (5-LO) at a test concentration of 1 $\mu$M

| Example # | Compound Name | Percent Inhibition of 5-LO at a test Conc. of (1 $\mu$M) |
|---|---|---|
| 2 | 5-[(1,1'-Biphenyl)-4-yl]-3,4-dihydroxy-5-methyl-2(5H)-furanone | 15 |
| 5 | 5-[(1,1'-Biphenyl)-4-yl]-3,4-dihydroxy-5-propyl-2(5H)-furanone | 68 |
| 6 | 5-[(1,1'-Biphenyl)-4-yl]-3,4-dihydroxy-5-(2-methylpropyl)-2(5H)-furanone | 70 |
| 7 | 5-[(1,1'-Biphenyl)-4-yl]-3,4-dihydroxy-5-phenyl-2(5H)-furanone | 61 |
| 8 | 3,4-Dihydroxy-5,5-diphenyl-2(5H)-furanone | 15 |
| 9 | 3,4-Dihydroxy-5-(4-isobutylphenyl)-5-(1-propyl)-2(5H)-furanone | 40 |
| 10 | 3,4-Dihydroxy-5-(4-isobutylphenyl)-5-phenyl-2(5H)-furanone | 64 |
| 11 | (S)-(+)-5-[(1,1'-Biphenyl)-4-yl]-3,4-dihydroxy-5-methyl-2(5H)-furanone | 59 |
| 12 | (R)-(−)-5-[(1,1'-Biphenyl)-4-yl]-3,4-dihydroxy-5-methyl-2(5H)-furanone | 60 |
| 13 | (R)-(−)-3,4-Dihydroxy-5-methyl-5-[4-(2-methylpropyl)phenyl]-2(5H)-furanone | 59 |

TABLE II-continued

The effect of various aci-reductones on 5-Lipoxygenase (5-LO) at a test concentration of 1 μM

| Example # | Compound Name | Percent Inhibition of 5-LO at a test Conc. of (1 μM) |
|---|---|---|
| 14 | (S)-(−)-3,4-Dihydroxy-5-methyl-5-[4-(2-methylpropyl)phenyl]-2(5H)-furanone | 50 |
| 15 | 3,4-Dihydroxy-5-[2-(4-phenoxy)phenoxyethyl]-2(5H)-furanone | 52 |
| 16 | 3,4-Dihydroxy-5-[2-(flavone-6-oxy)ethyl]-2(5H)-furanone | 54 |
| 17 | 5-[2-(Dibenzofuran-2-oxy)ethyl]-3,4-dihydroxy-2(5H)-furanone | 60 |
| 18 | 3,4-Dihydroxy-5-[2-(1-naphthoxy)ethyl]-2(5H)-furanone | 49 |
| 20 | 3,4-Dihydroxy-5-[2-(1,8-naphthosultam)-N-ethyl]-2(5H)-furanone | 38 |
| 21 | 3,4-Dihydroxy-5-[2-(diphenylmethane-2-oxy)ethyl]-2(5H)-furanone | 62 |
| 22 | 5-[2-((1,1'-Biphenyl)-4-oxy)ethyl]-3,4-dihydroxy-2(5H)-furanone | 55 |
| 24 | 3,4-Dihydroxy-5-[2-(4,5-diphenyl-1,3-isoxazole-2-thio)ethyl]-2(5H)-furanone | 71 |
| 25 | 3,4-Dihydroxy-5-[2-(naphthyl-1-thio)ethyl]-2(5H)-furanone | 56 |
| 26 | 3,4-Dihydroxy-5-[2-(naphthyl-2-thio)ethyl]-2(5H)-furanone | 54 |
| 29 | 3,4-Dihydroxy-5-[(4-(2-(2Z-hexenyl))phenyl)-3-butynyl]-2(5H)-furanone | 56 |
| 30 | 3,4-Dihydroxy-5-[(4-(2-phenylthio)methyl)phenyl)-3-butynyl]-2(5H)-furanone | 70 |
| 32 | 3,4-Dihydroxy-5-[4-(2-naphthyl)-3-butynyl]-2(5H)-furanone | 66 |
| 46 | 3,4-Dihydroxy-5-[2-(4-(4-fluorophenylmethyl)thiophene)-(3-butynyl)]-2(5H)-furanone | 91; $IC_{50}$ = 160 nM |

Nuclear factor-κB exists in the cytoplasm of most cells bound to a natural inhibitor protein IκB. In a complex cascade, extracellular stimulation by cytokines such as TNF-α or interleukin-1 (IL1), viruses, lipopolysaccharide (LPS) or UV-radiation results in the production of second messenger reactive oxygen species (ROS). Increased ROS concentrations are important mediators, which instigate the process of IκB disassociation from the NF-κB complex enabling NF-κB to migrate into the cell nucleus. Recent findings demonstrate that low levels of $H_2O_2$ activate NF-κB and that a number of antioxidants inhibit this activation process. The antioxidants pyrrolidone dithiocarbamate (PDTC) and N-acetyl-cysteine (NAC) inhibit both the $H_2O_2$ and extracellular cytokine-induced activation of NF-κB in a concentration dependent manner. Steroids such as dexamethasone are potent anti-inflammatory agents in part, because they stimulate the gene synthesis of IκB, leading to inhibition of NF-κB. The mechanism by which these aci-reductones block NF-κB nuclear translocation is not clear, but is likely related to their antioxidant properties. However, the possibility that they specifically interact with a biomolecule involved in NF-κB activation has not been disregarded.

| Test Compound | Concentration | % Inhibition |
|---|---|---|
| 3,4-Dihydroxy-5-[4-(2-naphthyl)-3-butynyl]-2(5H)-furanone | 30 nM | 90% |
| Reference Compounds Dexamethasone | 1000 nM | 60% |
| Pyrrolidone dithiocarbamate (PDTC) | 10,000 nM | 50% |
| N-Acetyl-cysteine (NAC) | 1000 nM | 0% |

Experiments measuring test agents effect on NF-κB nuclear membrane translocation were performed with NR8383 cells, which are transformed rat alveolar macrophages. Cells were treated simultaneously with LPS (1 μg/ml) and the test compounds (10 and 30 nM). In addition, some compounds were tested at doses of 10 and 30 μM. Untreated control cells and cells treated with LPS alone were tested in each experiment. Cells were harvested 6 hours after treatment. Nuclear proteins were extracted, frozen and quantified using the Bradford assay. Electrophoretic mobility shift assays (EMSA) were subsequently analyzed using a radio-labeled NF-κB probe. Nuclear proteins were reacted with the radiolabeled probe, run on a 5% polyacrylamide gel, and subjected to audoradiography. Specificity of protein binding for the NF-κB binding site was assayed by cold and non-specific competition using the LPS treated sample in each experiment. All EMSA were duplicated at least once to verify results. Laser densitometry of NF-κB bands was done on autoradiographs to quantify NF-κB binding activity.

The human T lymphoid cell line Jurkat was transfected with a response element lacZ reporter in which transcription of the β-galactosidase gene is directed by the binding site for the NF-κB transcription factor. The cell line containing κB-Z is stimulated with calcium ionophore A23187 and phorbol ester PMA; this stimulation is inhibited by the immunosuppressive drug cyclosporin A. In the screening assay transfected κB-Z Jurkat cells (1×10⁶ cells/assay well) are incubated with 2 μM A23187, 20 ng/mL PMA and test compound or vehicle in the well of a microplate for at least 4 hours according to the procedure of M. J. Lenardo and D. Baltimaore, NF-κB: a pleiotropic mediator of inducible and tissure specific gene control. *Cell* 58, 227–229, (1989). At the end of the incubation, the cells are spun down and resuspended in the buffer and FDG (fluorescein di-β-D-galactopyranoside) solution. The covered plates are further incubated in the dark for 16 hours at 25° C. The fluorescent product resulting from the end of reaction is read at 485/530 in a Cyto2300 fluorescence reader. Compounds were screened at 10 μM. The standard, cyclosporin A has an $IC_{50}$ of 50 nM in this assay.

TABLE III

The effect of various aci-reductones on Nuclear Factor-kappa B
Percent Inhibition (%)

| Example # | Compound Name | (PERCENT INHIBITION) NF-κB (10 μM) |
|---|---|---|
| 2 | 5-[(1,1'-Biphenyl)-4-yl]-3,4-dihydroxy-5-methyl-2(5H)-furanone | 90 |
| 5 | 5-[(1,1'-Biphenyl)-4-yl]-3,4-dihydroxy-5-propyl-2(5H)-furanone | 68 |
| 6 | 5-[(1,1'-Biphenyl)-4-yl]-3,4-dihydroxy-5-(2-methylpropyl)-2(5H)-furanone | 59 |
| 7 | 5-[(1,1'-Biphenyl)-4-yl]-3,4-dihydroxy-5-phenyl-2(5H)-furanone | 21 |
| 8 | 3,4-Dihydroxy-5,5-diphenyl-2(5H)-furanone | 33 |
| 9 | 3,4-Dihydroxy-5-(4-isobutylphenyl)-5-(1-propyl)-2(5H)-furanone | 26 |
| 10 | 3,4-Dihydroxy-5-(4-isobutylphenyl)-5-phenyl-2(5H)-furanone | 16 |
| 11 | (S)-(+)-5-[(1,1'-Biphenyl)-4-yl]-3,4-dihydroxy-5-methyl-2(5H)-furanone | 72 |
| 12 | (R)-(+)-5-[(1,1'-Biphenyl)-4-yl]-3,4-dihydroxy-5-methyl-2(5H)-furanone | 56 |
| 13 | (R)-(−)-3,4-Dihydroxy-5-methyl-5-[4-(2-methylpropyl)phenyl]-2(5H)-furanone | 49 |
| 14 | (S)-(+)-3,4-Dihydroxy-5-methyl-5-[4-(2-methylpropyl)phenyl]-2(5H)-furanone | 60 |
| 24 | 3,4-Dihydroxy-5-[2-(4,5-diphenyl-1,3-isoxazole-2-thio)ethyl]-2(5H)-furanone | 44 |
| 41 | 3,4-Dihydroxy-5-[2-(4-(4-fluorophenylmethyl)thiophene)-(3-butynyl)]-2(5H)-furanone | 61; $IC_{50} = 6\ \mu M$ |

The ability of the compounds of formula I to inhibit the action of various inflammatory cytokines make them useful in a wide variety of therapeutic methods. Specifically, their ability to mediate or inhibit the actions of TNF-α makes these compounds useful in the treatment of various invasive diseases, infections, and inflammatory states. Particularly important is the inhibition of the large amount of TNF produced during serious bacterial infections, which can trigger a state of shock and tissue injury (septic shock syndrome).

A further important use of the compounds of formula I is to inhibit the TNF which is known to mediate cachexia produced during chronic disease states. Thus, these compounds are particularly useful in adjunctive therapy for AIDS and cancer patients to reduce and/or ameliorate the consequences of cachexia produced during these chronic disease states.

A further specific method of treatment for which the compounds of the instant invention are particularly useful is in the treatment of rheumatoid arthritis wherein increased amounts of the inflammatory cytokines, TNF-α and IL-1 are present. By virtue of their ability to mediate and/or inhibit the action of these cytokines, inflammation and the severity of the disease state can be reduced or eliminated.

The compounds of the instant invention can also be utilized in the treatment of multiple sclerosis (MS), Crohn's disease and ulcerative colitis by inhibiting and the activity of the inflammatory cytokines which underlie these disease states.

The compounds of the invention may be formulated in a conventional manner, optionally together with one or more other active ingredients, for administration by any convenient route for example of oral, intravenous or intramuscular administration.

Thus, according to another aspect, the invention provides a pharmaceutical composition comprising a compound of formula I and/or a pharmaceutically acceptable salt thereof together with a pharmaceutically acceptable carrier or excipient.

For oral administration, the pharmaceutical composition may take the form of, for example, tablets, capsules, powders, solutions, syrups or suspensions prepared by conventional means with physiologically acceptable excipients.

The compounds may be formulated for intravenous or intramuscular administration in dry form for reconstitution before use, or as a sterile solution or suspension.

A proposed daily dose based on similar pharmacokinetic parameters to CHTA for administration to man is about 10 to 25 mg/kg, for example, 700 mg to 1 gm daily, which may be conveniently administered in 1 to 3 doses per day. The precise dose administered will, of course, depend on the age and condition of the patient.

The following examples are illustrative of the present invention.

EXAMPLES

General Methods. Unless otherwise noted all reagents were purchased from commercial suppliers and used as received. Melting points were determined in open capillaries with a Thomas-Hoover Uni-Melt Apparatus and are uncorrected. Nuclear magnetic resonance spectra were obtained with either an IBM-Bruker model NR/100 or Varian model 200 FT NMR spectrometer. Tetramethylsilane (TMS) in $CDCl_3$, $DMSO-d_6$, $acetone-d_6$, $CD_3OD$ or $D_2O$ was used as internal standard. Chemical shifts are reported on the δ scale with peak multiplicities: s, singlet; d, doublet; dd, doublet of doublets; ddd doublet of doublet of doublets; t, triplet; q, quartet, m, multiplet. Anhydrous solvents were purchased from Aldrich Chemical, Inc., Milwaukee, Wis. and used as such. Optical rotations were performed on a Perkin-Elmer model 241 polarimeter using a 10 cm, 1 mL cell. Elemental Analyses were performed by Quantitative Technologies, Inc., Whitehouse, N.J.

PREPARATION OF STARTING MATERIALS

EXAMPLE A

Ethyl 4-phenylbenzoylformate

A mixture of 77 g (500 mmol) of biphenyl and 68 mL (540 mmol) of ethyl oxalylchloride was dissolved in 300 mL of 1,2-dichloroethane and cooled with stirring to between 0° and 10° C. $AlCl_3$ (73 g, 550 mmol) was added at such a rate to maintain the reaction temperature below 15° C. The mixture was stirred at 10° C. for 1 hour and at 25° C. for 24 hours, then poured into 1000 mL of a ice cold 10% HCl solution. The aqueous suspension was extracted with 4×500 mL of ether and the combined ether extracts were washed with 100 mL of 10% HCl solution, 100 mL of brine, dried ($MgSO_4$) and concentrated to a yellow oil which was purified by chromatography over $SiO_2$ using initially acetone/hexanes (2/98) and increasing the polarity of the solvent to acetone/hexanes (10/90) upon elution of the nonpolar impurities to liberate 82 g (68% yield) of a yellow oil, which crystallized on standing.

EXAMPLE B

Ethyl 4-isobutylbenzoylformate

A mixture of 27 g (200 mmol) of isobutylbenzene and 24 mL (215 mmol) of ethyl oxalylchloride underwent Friedel-Crafts acylation reaction in an analogous fashion as described for the synthesis of ethyl 4-phenylbenzoylformate to yield 38 g (81% yield) of ethyl 4-isobutylbenzoylformate as a colorless oil.

EXAMPLE C

3-Benzyloxy-4-hydroxy-5-(2-hydroxy)ethyl-2(5H)-furanone

A. A solution of 10.0 g (98 mmol) of α-hydroxy-γ-butyrolactone in 100 mL of anhydrous THF under argon was cooled to 0–5° C. with magnetic stirring. Addition of 14 mL (110 mmol) of trimethylsilyl chloride and 16 mL (115 mmol) of triethylamine immediately produced a white precipitate. The suspension was warmed to room temperature and stirred for 4 hours. The suspension was poured into a separatory funnel containing 100 mL of $H_2O$ and 500 mL of ether. The organic layer was washed with 50 mL of $H_2O$, 50 mL of brine, dried ($MgSO_4$) and concentrated. Purification (Kugelrohr distillation) provided 14.7 g (90% yield) of α-trimethylsilyloxy-γ-butyrolactone bp 80–100° C. (8 mm Hg).

B. To a 500 mL 2-necked flask flame dried under argon and equipped with a magnetic stir bar, was added 200 mL of THF and 18.7 mL (89 mmol) of hexamethyldisilazide. The flask was cooled to –78° C. and 55.4 mL (89 mmol) of a 1.6 M nBuLi solution in hexanes was added with stirring over 15 min. The light yellow solution was stirred for an additional 15 min and 16.7 g (86 mmol) of ethyl benzyloxyacetate was added over 5 min. The solution was stirred for 20 min at –78° C., and 14.7 g (84.4 mmol) of α-silyloxy-γ-butyrolactone was added via syringe. The reaction mixture was quenched after 30 minutes by pouring into a mixture of 100 mL of 10% aqueous HCl solution and 500 mL of ether. The aqueous layer was separated and washed with 2×100 mL of ether. The combined ether extracts were washed with 50 mL of brine, dried ($MgSO_4$) and concentrated leaving a yellow oil, which was dried in vacuo for 15 hours.

C. The yellow oil was placed under argon, diluted with 400 mL of MeOH, cooled to 0° C. with stirring and 11.7 g (85 mmol) of anhydrous $K_2CO_3$ was added. After 30 minutes the suspension was concentrated to a volume of about 75 mL, diluted with 100 mL of $H_2O$ and 50 mL of saturated sodium bicarbonate solution, and washed with 2×100 mL of ether. The aqueous phase was acidified with 37% HCl solution to a pH near 1 and extracted with 10×150 mL of ether. The combined ether extracts were washed with 100 mL of brine, dried ($MgSO_4$) and concentrated to a yellow oil (18.7 g, 86%) which solidified upon standing. Recrystallization from benzene and hexanes provided 15.8 g, (75% yield) of 3-benzyloxy-4-hydroxy-5-(2-hydroxy)ethyl-2 (5H)-furanone as a white solid: mp 98–99° C., $^1$H NMR (acetone-$d_6$) δ 7.46–7.27 (m, 5H), 5.06 (s, 2H), 4.83 (t, J=6.3 Hz, 1H), 3.85–3.69 (m, 2H), 2.05–1.95 (m, 1H), 1.89–1.76 (m, 1H). Anal Calcd for $C_{13}H_{14}O_5$: C, 62.39; H, 5.64. Found: C, 62.51; H, 5.50.

EXAMPLE D 3,4-Dibenzyloxy-5-(2-hydroxyethyl)-2(5H)-furanone

A mixture of 1.25 g (5 mmol) of 3-benzyloxy-4-hydroxy-5-(2-hydroxyethyl)-2(5H)-furanone, 15 mL of THF, 871 μL (5.0 mmol) of diisopropylethylamine and 631 μL (5.2 mmol) of benzyl bromide were combined under argon. The reaction mixture was warmed to reflux for 5 hours, and upon cooling, a suspension formed which was poured into 50 mL of 5% aqueous HCl solution and extracted with 100 mL of ether. The ether fraction was separated and sequentially washed with 30 mL of 5% aqueous HCl, 30 mL of $H_2O$, 30 mL of saturated $NaHCO_3$ solution, 30 mL of $H_2O$, 30 mL of brine, dried ($MgSO_4$) and concentrated to a colorless oil. Purification over silica gel using EtOAc/hexanes (2/3) provided 3,4-dibenzyloxy-5-(2-hydroxyethyl)-2(5H)-furanone as a faint pink colored oil (1.0 g, 60% yield).

EXAMPLE E

3-Benzyloxy-4-hydroxy-5-(2-iodoethyl)-2(5H)-furanone

To an oven dried 250 mL round bottom flask flushed with argon was added 5.8 g (22 mmol) of $PPh_3$, 1.5 g (22 mmol) of imidazole and 80 mL of ether/$CH_3CN$ (3/1). The mixture was cooled in an ice water bath with magnetic stirring and 5.6 g (22 mmol) of iodine was added in 4 equal portions with vigorous stirring. The resulting slurry was warmed at room temperature for 20 minutes, cooled to 0° C., and 5.0 g (20 mmol) of 3-benzyloxy-4-hydroxy-5-(2-hydroxyethyl)-2 (5H)-furanone dissolved in 20 mL of $CH_3CN$/ether (1/1) was added in one portion and the remainder was rinsed in with 5 mL of ether. The mixture was stirred at 0° C. for 10 minutes, then at room temperature for 30 minutes and quenched by pouring into 150 mL of 10% HCl solution and extracting with 500 mL of ether/hexanes (1/1). The aqueous layer was separated and extracted with 100 mL of ether. The combined organic fractions were washed with 50 mL of $H_2O$ and extracted with 5×50 mL of saturated $NaHCO_3$ solution. The combined bicarbonate extracts were washed with 50 mL of ether/hexanes (1/1), acidified to pH below 2 with 10% HCl solution and extracted with 3×200 mL of ether. The combined ether extracts were washed with 100 mL of brine, dried ($MgSO_4$) and concentrated to give 6.7 g, (93% yield) of 3-benzyloxy-4-hydroxy-5-(2-iodoethyl)-2(5H)-furanone as a white solid, which was not further purified: mp 101–104° C., $^1$H NMR ($CDCl_3$) δ 7.40–7.27 (m, 5H), 5.06, (dd, J=11.4 Hz, 2H), 4.69 (dd, J=3.4, 8.0 Hz, 1H), 3.06 (t, J=7.3 Hz, 2H), 2.41–2.29 (m, 1H), 2.02–1.90 (m, 1H); $^{13}$C NMR ($CDCl_3$) δ 170.33, 160.61, 136.32, 128.77, 128.69, 128.58, 120.11, 75.76, 73.39, 35.77, –2.03; Anal Calcd for $C_{13}H_{13}O_4I$: C, 43.35; H, 3.64. Found: C, 43.94; H, 3.69.

EXAMPLE F 3,4-Dihydroxy-5-(2-iodoethyl)-2(5H)-furanone

To a dry flask flushed with argon was added 0.72 g (2.0 mmol) of 3-benzyloxy-4-hydroxy-5-(2-iodoethyl)-2(5H)-furanone and 10 mL of $CH_2Cl_2$. The solution was cooled with stirring in an ice-water bath, and 0.38 mL (4.0 mmol) of acetic anhydride and 0.34 mL (4.2 mmol) of pyridine were added. The ice bath was removed and the solution was stirred for 1 hour. All volatile substances were removed in vacuo (2 h at 1 mm Hg, 25° C.). Argon was introduced to the reaction flask and the residue was taken up in 20 mL of dry $CH_2Cl_2$, cooled to $-78°$ C. and 5.2 mL (2.6 mmol) of 1.0 M $BCl_3$ in $CH_2Cl_2$ was added with stirring. The reaction mixture was kept at $-78°$ C. for 1 hour and at room temperature for 30 minutes. The mixture was poured into 50 mL of brine and extracted with 3×30 mL of ether. The combined ether extracts were washed with 5 mL of $H_2O$ and extracted into saturated $NaHCO_3$ solution (3×15 mL). The bicarbonate fractions were pooled and washed with 15 mL of ether, acidified to pH 1 with 25% aqueous HCl solution, and extracted with 3×30 mL of ether. The ether extracts were combined and washed with 15 mL of brine, dried ($MgSO_4$) and concentrated to provide 360 mg (67% yield) of 3,4-dihydroxy-5-(2-iodoethyl)-2(5H)-furanone as a white crystalline solid: mp 150–151° C.; $^1$H NMR (acetone-$d_6$) δ 4.80 (dd, 1H, J=3.5, 8.0 Hz), 3.50–3.25 (m, 2H), 2.60–2.35 (m, 1H), 2.20–1.95 (m, 1H). Anal Calcd for $C_6H_7O_4I$: C, 26.69; H, 2.61. Found: C, 26.54; H, 2.59.

EXAMPLE G

3-Benzyloxy-5-(3-butyne)-4-hydroxy-2(5H)-furanone

To a flame-dried three-necked round bottom flask with magnetic stir bar, argon inlet, and septum containing 5.7 g (55.8 mmol) of 90% lithium acetylide ethylenediamine complex, was added 20 mL of HMPA. The suspension was stirred for 15 minutes at room temperature, cooled in an ice bath (acetone/$CO_2$) to between $-5°$ C. and $-10°$ C., and 6.7 g (18.6 mmol) of 3-benzyloxy-4-hydroxy-5-(2-iodoethyl)-2(5H)-furanone dissolved in 15 mL of HMPA was added over a two minute period. A dark brown-orange slurry formed and the temperature was maintained between 0° C. and $-5°$ C. for 30 minutes. The mixture was quenched by the careful addition of 150 mL of 10% aqueous HCl solution, which was immediately extracted with 2×200 mL of ether. The combined ether extracts were washed with 2×50 mL of 5% aqueous HCl solution and extracted with 4×50 mL of $NaHCO_3$ solution. The combined bicarbonate extracts were washed with 50 mL of ether, acidified with 20% aqueous HCl solution to pH 1 and extracted with 3×150 mL of ether. The combined ether extracts were washed with 50 mL of brine, dried ($MgSO_4$) and concentrated leaving 4.1 g (85% crude yield) of 3-benzyloxy-5-(3-butyne)-4-hydroxy-2(5H)-furanone as a yellow solid. This material was used without further purification in subsequent steps: mp 85–88° C.; $^1$H NMR (CDCl$_3$) δ 7.38–7.26 (m, 5H), 5.06, (q, $J_{ab}$=11.6 Hz, 2H), 4.75 (dd, J=3.5, 8.1 Hz, 1H), 2.27–2.20 (m, 2H), 2.12–2.01 (m, 1H), 1.98 (t, J=2.6 Hz, 1H), 1.73–1.62 (m, 1H); $^{13}$C NMR (CDCl$_3$) δ 169.93, 160.90, 136.39, 128.77, 128.73, 128.64, 120.13, 82.31, 74.30, 73.43, 69.71, 30.78, 13.72.

EXAMPLE H 5-(3-Butyne)-3,4-dihydroxy-2(5H)-furanone

An oven dried 250 mL flask equipped with a magnetic stir bar was flushed with argon and charged with 2.6 g (10.0 mmol) of 3-benzyloxy-5-(3-butyne)-4-hydroxy-2 (5H)-furanone and 50 mL of anhydrous $CH_2Cl_2$. The solution was cooled in an ice bath to 5° C. with magnetic stirring and 1.9 mL (20.0 mmol) of acetic anhydride was added followed by 1.7 mL (21 mmol) of pyridine. The ice bath was removed after 1 hour, and the mixture was concentrated on a rotary evaporator and dried at 0.5 mm Hg at 25° C. for 12 hours. Argon was introduced followed by 100 mL of dry $CH_2Cl_2$. The solution was cooled to $-78°$ C. with stirring and 25 mL (25 mmol) of 1.0 M BCl3 in $CH_2Cl_2$ was added. The reaction mixture was allowed to gradually warm to 10° C. over a 2 hour period and maintained at 10° C. for 1 hour. The mixture was poured into 50 mL of brine and extracted with 4×100 mL of ether. The combined ether fractions were extracted with 3×25 mL of saturated $NaHCO_3$ solution. The combined bicarbonate extracts were washed with 25 mL of ether and acidified to pH 1 with aqueous HCl solution and extracted with 5×100 mL of ether. The combined ether washes were dried ($MgSO_4$) and filtered through 100 g of silica gel to remove a polar impurity using 1 L of ether as eluant. Removal of solvent in vacuo left 1.4 g (80% yield) of 5-(3-butyne)-3,4-dihydroxy-2(5H)-furanone as an off white solid: mp 124–128° C. dec.; $^1$H NMR (acetone-$d_6$) δ 4.79 (dd, J=3.4, 8.3 Hz, 1H) 2.42 (t, J=2.6 Hz, 1H) 2.37–2.30 (m, 2H), 2.20–2.09 (m, 1H), 1.81–1.67 (m, 1H); $^{13}$C NMR (acetone-$d_6$) δ 170, 153.7, 119, 83.4, 74.7, 70.9, 32.4, 14.4; Anal Calcd for $C_8H_8O_4$: C, 57.14; H, 4.79. Found: C, 57.04; H, 5.01.

EXAMPLE I 2-(2Z-Hexenyl)iodobenzene

A dry 25 mL 2-necked flask equipped with a magnetic stir bar, argon inlet and septum was cooled to 0° C. and 3 mL of 1.0 M $BH_3$ in THF was added. Cyclohexene, 607 μL (6 mmol) was added via syringe and the suspension stirred at 0–5° C. for 35 minutes. 2-Hexynyliodobenzene$_5$ (0.852 g, 3.0 mmol) was added to the reaction mixture dropwise over a 5 minute period, the ice bath was removed and the yellow reaction mixture stirred at room temperature for 1 hour. The solution was subsequently cooled in an ice bath, and 1.4 mL (25 mmol) of glacial AcOH was added. The mixture stirred at room temperature for 1 hour, was poured into 75 mL of $H_2O$, and extracted with 3×30 mL of hexanes. The combined hexanes fractions were washed with 25 mL of $H_2O$, 25 mL of saturated $NaHCO_3$ solution, 25 mL of $H_2O$, 2×20 mL of brine, dried ($MgSO_4$) and concentrated to an oil (do not warm above 30° C. to avoid isomerization of the double bond). Purification over 40 g of silica gel using hexanes as eluant provided 670 mg (78%) of 2-(2Z-hexenyl) iodobenzene as a colorless oil: $^1$H NMR (CDCl$_3$) δ 7.82 (d, J=7.8 Hz, 1H), 7.30–7.20 (m, 2H), 6.91–6.86 (m, 1H), 5.6–5.46 (m, 2H), 3.47 (d, J=6.5 Hz, 2H), 2.17–2.10 (m, 2H), 1.49–1.37 (m, 2H), 0.94 (t, J=7.3 Hz, 3H); $^{13}$C NMR (CDCl$_3$) δ 143.8, 139.3, 131.8, 129.2, 128.3, 127.7, 126.6, 100.8, 38.8, 29.6, 22.7, 13.9; Anal Calcd for $C_{12}H_{15}I$: C, 50.37; H, 5.28. Found: C, 49.97; H, 5.24.

SYNTHESIS OF COMPOUNDS OF THE INVENTION

EXAMPLE 1

3,4-Dihydroxy-5-methyl-5-phenyl-2(5H)-furanone

A. To a 2-necked flask flame dried under argon with septum and charged with a solution of 3.6 g (20 mmol) of ethyl benzoylformate in 50 mL of anhydrous THF at $-30°$ C. was slowly added 7 mL (21 mmol) of a 3.0 M solution of methylmagnesium iodide. The reaction mixture was stirred at 0° C. for 45 minutes, then at room temperature for 30 minutes and again cooled to 0° C. Benzyloxyacetyl chloride (3.4 mL, 21 mmol) was added and the reaction mixture was stirred at room temperature for 1 hour, cooled to $-78°$ C. and 33 mL of a 1.5 M solution of LDA in THF was added with rapid stirring. The mixture was worked up after 1 hour by the addition of 100 mL of aqueous 10% HCl solution and 300 mL of ether. The layers were separated and the organic phase was washed with 50 mL aqueous 10% HCl solution, 30 mL of $H_2O$, and extracted with 3×40 mL of saturated $NaHCO_3$ solution. The bicarbonate extracts were combined and washed with 40 mL of ether, acidified to pH 1 with 10% aqueous HCl solution, and extracted with 2×80 mL of ether. The organic fractions were combined, washed with 25 mL of $H_2O$, 25 mL of brine, dried ($MgSO_4$), and concentrated leaving 1.2 g (20% yield) of 4-hydroxy-5-methyl-5-phenyl-3-phenylmethoxy-2-(5H)-furanone as a yellow oil.

B. The 4-hydroxy-5-methyl-5-phenyl-3-phenylmethoxy-2-(5H)-furanone (1.2 g) was subjected to hydrogenation over 100 mg of 5% $Pd/BaSO_4$ in 100 mL of MeOH at room temperature and under 30 psi H2. The reaction was monitored periodically by TLC analysis. The suspension was filtered through two #1 filter papers, concentrated to a white solid and recrystallized from $MeOH/H_2O$ to give 3,4-dihydroxy-5-methyl-5-phenyl-2(5H)-furanone as a white crystalline material: mp 173–175° C. dec. $^1H$ NMR (acetone-$d_6$) δ 7.53–7.36 (m, 5H), 1.84 (s, 3H). Anal Calcd for $C_{11}H_{10}O_4$+0.125 $H_2O$: C, 63.38; H, 4.96. Found: C, 63.30; H, 4.96.

EXAMPLE 2

5-[(1,1'-Biphenyl)-4-yl]-3,4-dihydroxy-5-methyl-2 (5H)-furanone

A. A total of 3.4 mL (10.2 mmol) of 3.0 M methylmagnesium iodide in THF was added to a THF solution of 2.4 g (10 mmol) of ethyl 4-phenylbenzoylformate in an analogous manner as described for the synthesis of 3,4-dihydroxy-5-methyl-5-phenyl-2(5H)-furanone to give prior to hydrogenolysis, 1.1 g (30% yield) of 5-[(1,1'-biphenyl)-4-yl]-3-phenylmethoxy-4-hydroxy-5-methyl-2(5H)-furanone as a white granular solid: m.p. 182–183° C. (benzene/hexanes) $^1H$ NMR ($CDCl_3$) δ 7.56–7.26 (m, 14H), 5.10 (ab quartet, 2H, J=11.4 Hz), 1.79 (s, 3H). $^{13}C$ NMR ($CDCl_3$) δ 168.5, 163.8, 141.5, 140.3, 137.0, 136.3, 129.0, 128.8, 128.8, 128.8, 127.6, 127.2, 127.1, 125.6, 119.0, 81.1, 73.5, 24.3. Anal Calcd for $C_{24}H_{20}O_4$: C, 77.40; H, 5.41. Found: C, 77.99; H, 5.61.

B. Hydrogenolysis of 500 mg of the 5-[(1,1'-biphenyl)-4-yl]-3-phenylmethoxy-4-hydroxy-5-methyl-2(5H)-furanone was performed in a similar manner as described in the synthesis of 3,4-dihydroxy-5-methyl-5-phenyl-2(5H)-furanone to provided 240 mg (63% yield) of 5-[(1,1'-biphenyl)-4-yl]-3,4-dihydroxy-5-methyl-2(5H)-furanone as a white powder: mp 206–212° C. dec. ($MeOH/H_2O$), $^1H$ NMR (acetone-$d_6$) δ 7.69–7.33 (m, 9H), 1.88 (s, 3H). $^{13}C$ NMR (acetone-d6) δ 169.5, 157.1, 141.6, 141.0, 139.8, 129.6, 128.3, 127.6, 127.6, 126.6, 117.9, 81.2, 24.5. Anal Calcd for $C_{17}H_{14}O_4$: C, 72.33; H, 5.00. Found: C, 72.07; H, 5.14.

EXAMPLE 3

3,4-Dihydroxy-5-methyl-5-[4-(2-methylpropyl) phenyl]-2(5H)-furanone

A. A total of 3.4 mL (10.2 mmol) of 3.0 M methylmagnesium iodide in THF was added to a THF solution of 2.34 g (10 mmol) of ethyl 4-isobutylbenzoylformate in an analogous manner as described for the synthesis of 3,4-dihydroxy-5-methyl-5-phenyl-2(5H)-furanone to give prior to hydrogenolysis 4-hydroxy-5-methyl-5-[4-(2-methylpropyl)phenyl]-3-phenylmethoxy-2(5H)-furanone in 45% yield as a yellow oil. $^1H$ NMR ($CDCl_3$) δ 7.37–7.02 (m, 9H), 5.01 (s, 2H), 2.42 (d, 2H, J=7.2 Hz), 1.86–1.77 (m, 1H), 1.72 (s, 3H), 0.87 (d, 6H, J=6.6 Hz). $^{13}C$ NMR ($CDCl_3$) δ 170.0, 165.1, 142.1, 136.3, 135.2, 129.2, 128.9, 128.6, 127.2, 125.0, 118.6, 81.7, 73.5, 45.0, 30.2, 24.1, 22.4. Anal Calcd for $C_{22}H_{24}O_4$+0.5 $H_2O$: C, 73.11; H, 6.97. Found: C, 72.92; H, 6.87.

B. Hydrogenolysis of 800 mg (2.3 mmol) of 4-hydroxy-5-methyl-5-[4-(2-methylpropyl)phenyl]-3-phenylmethoxy-2(5H)-furanone was performed in a similar manner as described in the preparation of 3,4-dihydroxy-5-methyl-5-phenyl-2(5H)-furanone to provided 500 mg (84% yield) of 3,4-dihydroxy-5-methyl-5-[4-(2-methylpropyl)phenyl]-2 (5H)-furanone as a light yellow crystalline material: mp 135–150° C. dec. $^1H$ NMR (acetone-$d_6$) δ 7.40–7.17 (m, 4H), 2.46 (d, 2H, J=7.1 Hz), 1.87–1.82 (m, 1H), 1.82 (s, 3H), 0.87 (d, 6H, J=6.6 Hz). $^{13}C$ NMR (acetone-$d_6$) δ 169.5, 157.2, 142.4, 138.0, 129.8, 125.9, 117.9, 81.3, 45.3, 30.8, 24.5. 22.5. Anal Calcd for $C_{15}H_{18}O_4$+0.25 $H_2O$: C, 67.53; H, 6.99. Found: C, 67.78; H, 7.09.

EXAMPLE 4

5-(4-Chlorophenyl)-3,4-dihydroxy-5-methyl-2(5H)-furanone

A. A total of 3.4 mL (10.2 mmol) of 3.0 M methylmagnesium iodide was added to a solution of 2.34 g (10 mmol) of ethyl 4-chlorobenzoylformate in THF in an analogous manner as described for the synthesis of 3,4-dihydroxy-5-methyl-5-phenyl-2 (5H)-furanone to give prior to hydrogenolysis 1.3 g (40% yield) of 5-(4-chlorophenyl)-4-hydroxy-5-methyl-3-phenylmethoxy-2(5H)-furanone as a yellow oil: $^1H$ NMR ($CDCl_3$) δ 7.37–7.21 (m, 9H), 5.10 (s, 2H), 1.73 (s, 3H).

B. Hydrogenolysis of 330 mg of 5-(4-chlorophenyl)-4-hydroxy-5-methyl-3-phenylmethoxy-2(5H)-furanone was performed in a similar manner as described in the preparation of 3,4-dihydroxy-5-methyl-5-phenyl-2(5H)-furanone to provided 110 mg (46% yield) of 5-(4-chlorophenyl)-3,4-dihydroxy-5-methyl-2(5H)-furanone a light tan solid: mp 154–155° C. dec. (benzene/hexanes) $^1H$ NMR (acetone-$d_6$) δ 7.52–7.34 (m, 4H), 1.82 (s, 3H). $^{13}C$ NMR (acetone-$d_6$) δ 169.0, 156.6, 139.8, 134.3, 129.2, 127.8, 117.9, 80.8, 24.6. Anal Calcd for $C_{11}H_9ClO_4$: C, 54.90; H, 3.77. Found: C, 54.74; H, 4.08.

EXAMPLE 5

5-[(1,1'-Biphenyl)-4-yl]-3,4-dihydroxy-5-propyl-2 (5H)-furanone

A. A total of 5.2 mL (10.4 mmol) of 2.0 M n-propylmagnesium bromide was added to a solution of 2.4 g (10 mmol) of ethyl 4-phenylbenzoylformate in THF in an analogous manner as described for the synthesis of 3,4-dihydroxy-5-methyl-5-phenyl-2(5H)-furanone to give prior to hydrogenolysis 0.30 g (8% yield) of 5-[(1,1'-biphenyl)-4-yl]-4-hydroxy-3-phenylmethoxy-5-propyl-2(5H)-furanone as an off white solid after crystallization from $CHCl_3$ and hexanes.

B. Hydrogenolysis of 250 mg of 5-[(1,1'-biphenyl)-4-yl]-4-hydroxy-3-phenylmethoxy-5-propyl-2(5H)-furanone was performed in a similar manner as described in the preparation of 3,4-dihydroxy-5-methyl-5-phenyl-2(5H)-furanone to provided 100 mg (52% yield) of a white powder: mp 203–204° C. dec. (acetone/$CHCl_3$/hexanes). $^1H$ NMR (acetone-$d_6$) δ 7.65–7.40 (m, 9H), 2.25–1.95 (m, 2H), 1.45–1.10 (m, 2H), 0.95 (t, J=6.9 Hz, 3H). Anal Calcd for $C_{19}H_{18}O_4$+0.125 $H_2O$: C, 73.01; H, 5.88. Found: C, 72.99; H, 5.86.

EXAMPLE 6

5-[(1,1'-Biphenyl)-4-yl]-3,4-dihydroxy-5-(2-methylpropyl)-2(5H)-furanone

A. A total of 5.2 mL (10.4 mmol) of 2.0 M isobutylmagnesium bromide was added to a solution of 2.4 g (10 mmol) of ethyl 4-phenylbenzoylformate in THF in an analogous manner as described for the synthesis of 3,4-dihydroxy-5-methyl-5-phenyl-2(5H)-furanone to give prior to hydrogenolysis 0.35 g (8% yield) of 5-[(1,1'-biphenyl)-4-yl]-4-hydroxy-3-phenylmethoxy-5-(2-methylpropyl)-2(5H)-furanone as an off white solid after crystallization from CHCl$_3$ and hexanes.

B. Hydrogenolysis of 350 mg of 5-[(1,1'-biphenyl)-4-yl]-4-hydroxy-3-phenylmethoxy-5-(2-methylpropyl)-2(5H)-furanone was performed in a similar manner as described in the preparation of 3,4-dihydroxy-5-methyl-5-phenyl-2(5H)-furanone to provide 190 mg (69% yield) of a white powder: mp 198–199° C. dec. (CHCl$_3$/hexanes). $^1$H NMR (acetone-d$_6$) δ 7.73–7.34 (m, 9H), 2.44–2.28 (m, 1H), 1.50–0.80 (m,8H). $^{13}$C NMR (acetone-d$_6$) δ 169.21, 155.47, 140.81, 139.57, 129.17, 127.73, 127.18, 127.08, 126.04, 118.47, 86.01, 40.66, 23.72, 12.11, 11.87. Anal Calcd for C$_{20}$H$_{20}$O$_4$+0.125 H$_2$O: C, 73.55; H, 6.25. Found: C, 73.25; H, 6.36.

EXAMPLE 7

5-[(1,1'-Biphenyl)-4-yl]-3,4-dihydroxy-5-phenyl-2(5H)-furanone

A. A total of 3.4 mL (10.2 mmol) of 3.0 M phenylmagnesium bromide was added to a solution of 2.4 g (10 mmol) of ethyl 4-phenylbenzoylformate in THF in an analogous manner as described for the synthesis of 3,4-dihydroxy-5-methyl-5-phenyl-2(5H)-furanone to give prior to hydrogenolysis 0.88 g (20% yield) of 5-[(1,1'-biphenyl)-4-yl]-4-hydroxy-3-phenylmethoxy-5-phenyl-2(5H)-furanone as an off white solid: mp 190–195° C. (CHCl$_3$/hexanes).

B. Hydrogenolysis of 500 mg of 5-[(1,1'-biphenyl)-4-yl]-4-hydroxy-3-phenylmethoxy-5-phenyl-2(5H)-furanone was performed in a similar manner as described in the preparation of 3,4-dihydroxy-5-methyl-5-phenyl-2(5H)-furanone to provide 150 mg (38% yield) of 5-[(1,1'-biphenyl)-4-yl]-3,4-dihydroxy-5-phenyl-2(5H)-furanone as colorless needles: mp 188–191° C. dec. (CHCl$_3$/hexanes). $^1$H NMR (acetone-d$_6$) δ 7.75–7.36 (m, 14H). $^{13}$C NMR (acetone-d$_6$) δ 168.34, 154.84, 141.50, 140.66, 140.30, 139.42, 129.18, 128.74, 128.59, 127.92, 127.40, 127.25, 127.07, 119.45, 84.59. Anal Calcd for C$_{22}$H$_{16}$O$_4$: C, 76.73; H, 4.68. Found: C, 76.44; H, 4.50.

EXAMPLE 8

3,4-Dihydroxy-5,5-diphenyl-2(5H)-furanone

A. A total of 3.5 mL (10.5 mmol) of 3.0 M phenylmagnesium bromide was added to a solution of 1. 6 mL (10 mmol) of ethyl benzoylformate in THF in an analogous manner as described for the synthesis of 3,4-dihydroxy-5-methyl-5-phenyl-2(5H)-furanone to give 5,5-diphenyl-4-hydroxy-3-phenylmethoxy-2(5H)-furanone as an oil, which was purified over SiO$_2$ using acetone/hexanes (3/7).

B. Hydrogenolysis of 5,5-diphenyl-4-hydroxy-3-phenylmethoxy-2(5H)-furanone was performed in a similar manner as described in the preparation of 3,4-dihydroxy-5-methyl-5-phenyl-2(5H)-furanone to provide 150 mg (5.6% overall yield) of 3,4-dihydroxy-5,5-diphenyl-2(5H)-furanone as colorless needles: mp 192–193° C. dec. (CHCl$_3$/hexanes). $^1$H NMR (acetone-d$_6$) δ 7.41 (s, 10H). $^{13}$C NMR (acetone-d$_6$) δ 168.38, 154.92, 140.44, 128.72, 128.58, 127.43, 119.46, 84.74. Anal Calcd for C$_{16}$H$_{12}$O$_4$+0.25 H$_2$O C, 70.46; H, 4.62. Found: C, 70.42; H, 4.52.

EXAMPLE 9

3,4-Dihydroxy-5-(4-isobutylphenyl)-5-(1-propyl)-2(5H)-furanone

A. A total of 5.2 mL (10.4 mmol) of 2.0 M 1-propylmagnesium bromide was added to a solution of 2.3 g (10 mmol) of ethyl 4-isobutylbenzoylformate in THF in an analogous manner as described for the synthesis of 3,4-dihydroxy-5-methyl-5-phenyl-2(5H)-furanone to provide 4-hydroxy-5-(4-isobutylphenyl)-3-phenylmethoxy-5-(1-propyl)-2(5H)-furanone as an oil, which was purified over SiO$_2$ using acetone/hexanes (1/4).

B. Hydrogenolysis of 4-hydroxy-5-(4-isobutylphenyl)-3-phenylmethoxy-5-(1-propyl)-2(5H)-furanone was performed in a similar manner as described in the preparation of 3,4-dihydroxy-5-methyl-5-phenyl-2(5H)-furanone to provide 200 mg (6.9% yield) of 3,4-dihydroxy-5-(4-isobutylphenyl)-5-(1-propyl)-2(5H)-furanone as an oil, which was purified by preparative TLC using hexanes/acetone/acetic acid (70/29/1) as eluant: $^1$H NMR (acetone-d$_6$) δ 7.48–7.13 (m, 4H), 2.47 (d, J=10.3 Hz, 2H), 2.10–1.66 (m, 1H), 1.29–0.85 (m, 13H). $^{13}$C NMR (acetone-d$_6$) δ 169.20, 155.54, 141.58, 137.91, 129.24, 125.32, 118.25, 83.37, 45.02, 39.60, 30.26, 22.03, 16.84, 13.63. Anal Calcd for C$_{17}$H$_{22}$O$_4$: C, 70.32; H, 7.64. Found: C, 70.01; H, 7.61.

EXAMPLE 10

3,4-Dihydroxy-5-(4-isobutylphenyl)-5-phenyl-2(5H)-furanone

A. A total of 3.5 mL (10.5 mmol) of 3.0 M phenylmagnesium bromide was added to a solution of 2.3 g (10 mmol) of ethyl 4-isobutylbenzoylformate in THF in an analogous manner as described for the synthesis of 3,4-dihydroxy-5-methyl-5-phenyl-2(5H)-furanone to provide an oil, which was purified over 400 g of SiO$_2$ by eluting with 500 mL of CHCl$_3$, 500 mL of EtOH/CHCl$_3$ (3/97) and 500 mL of EtOH/CHCl$_3$ (8/92) to provide 1.2 g (29% yield) of 4-hydroxy-5-(4-isobutylphenyl)-5-phenyl-3-phenylmethoxy-2(5H)-furanone as a tan powder recrystallized from CHCl$_3$ and hexanes.

B. Hydrogenolysis of 500 mg (1.2 mmol) of 4-hydroxy-5-(4-isobutylphenyl)-5-phenyl-3-phenylmethoxy-2(5H)-furanone was performed in a similar manner as described in the preparation of 3,4-dihydroxy-5-methyl-5-phenyl-2(5H)-furanone to provide 200 mg (51% yield) of 3,4-dihydroxy-5-(4-isobutylphenyl)-5-phenyl-2(5H)-furanone as a white powder: mp 138–139° C. (CHCl$_3$/hexanes). $^1$H NMR (acetone-d$_6$) δ 7.40–7.15 (m, 9H), 2.49 (d, J=7.1 Hz, 2H), 1.94–1.74 (m, 1H), 0.89 (d, J=6.5 Hz, 6H). Anal Calcd for C$_{20}$H$_{20}$O$_4$: C, 74.1; H, 6.2. Found: C, 73.7; H, 6.3.

EXAMPLE 11

(S)-(+)-5-[(1,1'-Biphenyl)-4-yl]-3,4-dihydroxy-5-methyl-2(5H)-furanone

A. To a flame dried 500 mL flask flushed with N$_2$, was added 24 g (100 mmol) of ethyl 4-phenylbenzoylformate and 300 mL of anhydrous THF. The solution was cooled with stirring to −25° C. and 37 mL (110 mmol) of a 3.0 M solution of methylmagnesium iodide was added at a rate to maintain the reaction temperature below −10° C. The reaction progress was monitored by TLC and upon disappearance of starting material, 100 mL of saturated $NH_4Cl$ solution and 200 mL of ether were added. The organic layer was separated and washed with 2×50 mL of brine, dried ($MgSO_4$) and concentrated leaving racemic ethyl 2-[(1,1'-biphenyl)-4-yl]-2-hydroxypropionate as an oil.

B. The crude ethyl 2-[(1,1'-biphenyl)-4-yl]-2-hydroxypropionate was saponified by treating with 100 mL of ethanol and 100 mL of 4.0 M NaOH solution. The suspension was stirred for 3 hours, after which a clear solution formed The solution was concentrated, diluted with 150 mL of $H_2O$, washed with 2×50 mL of ether, and acidified to pH 1 with 10% HCl solution. The aqueous phase was extracted with 3×100 mL portions of ether and the combined ether extracts were washed with 50 mL of $H_2O$, 50 mL of brine, dried ($MgSO_4$) and concentrated leaving 18.3 g (72% yield) of racemic 2-[(1,1'-biphenyl)-4-yl]-2-hydroxypropionic acid as a white solid after was recrystallization from $CHCl_3$ and hexanes.

C. Racemic 2-[(1,1'-biphenyl)-4-yl]-2-hydroxypropionic acid 12.1 g (50 mmol) was resolved by dissolving in 225 mL of a 2:2:1 mixture of isopropanol:benzene:hexanes. The solution was warmed to reflux and 6.9 g (50 mmol) of (R)-(−)-phenylglycinol was added in one portion. The mixture was allowed to cool slowly over 15 hours during which white crystals formed, which were isolated by filtration and washed with several small portions of isopropanol. The isolated white solid was recrystallized four additional times from isopropanol until a constant melting point of 189.5–191° C. was observed, leaving 4.3 g (45.3% yield for the resolution) of diastereomerically pure (S)-(+)-2-[(1,1'-biphenyl)-4-yl]-2-hydroxypropionate (R)-(−)-phenylglycinol salt.

D. Diastereomerically pure (S)-(+)-2-[(1,1'-biphenyl)-4-yl]-2-hydroxypropionate (R)-(−)-phenylglycinol salt (1.9 g, 5 mmol) was added to a separatory funnel containing 70 mL of 15% aqueous HCl solution and 150 mL of ether. The suspension was shaken until completely solvated, and the aqueous layer was separated. The ether portion was washed with 2×50 mL of 15% aqueous HCl solution, 50 mL of $H_2O$, 50 mL of brine, dried ($MgSO_4$) and filtered into a 500 mL flask. The ether solution was cooled in an ice bath and a freshly prepared etheral solution of diazomethane was added with stirring until the yellow color of the reagent persisted. The solution was concentrated leaving 1.3 g (99%) of methyl (S)-(+)-2-[(1,1'-biphenyl)-4-yl]-2-hydroxypropionate as a white crystalline material.

E. In a dry flask under argon, were mixed 1.3 g (5 mmol) of methyl (S)-(+)-2-[(1,1'-biphenyl)-4-yl]-2-hydroxypropionate, 1.7 mL (10 mmol) of 95% benzyloxyacetyl chloride and 6.1 mL of pyridine. The reaction stirred for 48 hours and was quenched by pouring into 100 mL of 10% aqueous HCl and 200 mL of ether. The ether fraction was separated and washed with 50 mL of 10% aqueous HCl, 50 mL of $H_2O$, 2×50 mL of $NaHCO_3$ solution, 50 mL of $H_2O$, 50 mL of brine, dried ($MgSO_4$) and concentrated. The product was purified over 250 g of $SiO_2$ using initially EtOAc/hexanes (1/9) followed by EtOAc/hexanes (1.5/8.5) as eluant to yield 1.5 g (80% yield) of methyl (S)-(+)-2-[(1,1'-biphenyl)-4-yl]-2-(2-phenylmethoxyacetoyl)oxypropionate.

F. (S)-(+)-2-[(1,1'-Biphenyl)-4-yl]-2-(2-phenylmethoxyacetoyl)oxypropionate (1.5 g, 4 mmol) was dissolved in 10 mL of anhydrous THF and added to 33 mL of a 0.3 M solution of LiHMDA in THF at −78° C. The light yellow solution stirred for 45 minutes and was quenched by the addition of 30 mL of 10% aqueous HCl solution. The mixture was taken into 200 mL of ether and washed with 30 mL of 10% aqueous HCl solution, 30 mL of $H_2O$, 30 mL of brine, dried ($MgSO_4$) and concentrated. The resultant oil was taken up in 50 mL of ether and extracted with 4×30 mL of saturated $NaHCO_3$ solution. The combined $NaHCO_3$ fractions were washed with 25 mL of ether, acidified to pH below 1 with 10% aqueous HCl solution and extracted with 2×100 mL of ether. The combined ether extracts were washed with 25 mL of $H_2O$, 25 mL of brine, dried ($MgSO_4$) and concentrated to give (S)-(+)-5-[(1,1'-biphenyl)-4-yl]-4-hydroxy-5-methyl-3-phenylmethoxy-2(5H)-furanone.

G. The (S)-(+)-5-[(1,1'-biphenyl)-4-yl]-4-hydroxy-5-methyl-3-phenylmethoxy-2(5H)-furanone was subjected to hydrogenation over 100 mg of 5% $Pd/BaSO_4$ in 100 mL of MeOH at room temperature under 30 psi of $H_2$. The reaction was monitored periodically by TLC analysis. Upon reaction completion, the suspension was filtered through two #1 filter papers, concentrated and recrystallized from $CHCl_3$ and hexanes to provide 300 mg (20% overall yield from methyl (S)-(+)-2-[(1,1'-biphenyl)-4-yl]-2-hydroxypropionate) of (S)-(+)-5-[(1,1'-biphenyl)-4-yl]-3,4-dihydroxy-5-methyl-2(5H)-furanone as a light weight white crystalline material: mp 204–206° C. dec.; $[\alpha]^{25}_D$ +121° (c=0.66; MeOH); $^1$H NMR (acetone-$d_6$) δ 7.72–7.41 (m, 9H), 1.89 (s, 3H). Anal Calcd for $C_{17}H_{14}O_4$+0.75 $H_2O$: C, 69.03; H, 5.28. Found: C, 68.69; H, 4.95.

EXAMPLE 12

(R)-(−)-5-[(1,1'-Biphenyl)-4-yl]-3,4-dihydroxy-5-methyl-2(5H)-furanone

A. The combined filtrates from the resolution of racemic 2-[(1,1'-biphenyl)-4-yl]-2-hydroxypropionic acid with (R)-(−)-phenylglycinol (example 11, section C) were concentrated to a thick brown paste and partitioned between 100 mL of 20% HCl solution and 400 mL of ether. The aqueous phase was separated and the ether layer was subsequently washed with 4×30 mL of 20% HCl solution, 50 mL of brine, dried ($MgSO_4$) and concentrated. A total of 8.5 g (35 mmol) of 2-[(1,1'-biphenyl)-4-yl]-2-hydroxypropionic acid was recovered and dissolved in 300 mL of isopropanol by warming to reflux and 4.5 g (35 mmol) of (S)-(+)-phenylglycinol was added. The diastereomeric salts were allowed to crystallize at 25° C. over a period of 72 hours and isolated by filtration and washed with 2×40 mL of isopropanol to provide 6.7 g of light brown crystals. Two subsequent recrystallizations from isopropanol provided 3.6 g of the diastereomerically pure salt of (R)-(−)-2-[(1,1'-biphenyl)-4-yl]-2-hydroxypropionic acid with (S)-(+)-phenylglycinol.

B. (R)-(−)-5-[(1,1'-Biphenyl)-4-yl]-3,4-dihydroxy-5-methyl-2(5H)-furanone was prepared in an analogous manner as described for (S)-(+)-5-[(1, 1'-biphenyl)-4-yl]- 3,4-dihydroxy-5-methyl-2(5H)-furanone starting with 1.9 g (5.0 mmol) of the diastereomerically pure salt of (R)-(−)-2-[(1, 1'-biphenyl)-4-yl]-2-hydroxypropionic acid and (S)-(+)-phenylglycinol to provide 280 mg (19% yield) of (R)-(−)-5-[(1,1'-biphenyl)-4-yl]-3,4-dihydroxy-5-methyl-2(5H)-furanone as a white crystalline material: mp 197–199° C. dec. ($CHCl_3$/hexanes); $[\alpha]^{25}_D$ −182° (c=1.42; MeOH); $^1$H NMR (acetone-$d_6$) δ 7.65–7.41 (m, 9H), 1.89 (s, 3H). Anal Calcd for $C_{17}H_{14}O_4$+0.25 $H_2O$: C, 71.20; H, 5.10. Found: C, 71.19; H, 4.74.

EXAMPLE 13

(R)-(−)-3,4-Dihydroxy-5-methyl-5-[4-(2-methylpropyl)phenyl]-2(5H)-furanone (R)-(−)-3,4-Dihydroxy-5-methyl-5-[4-(2-methylpropyl)phenyl]-2(5H)-furanone was synthesized in an analogous manner used for the production of (S)-(+)-5-[(1,1'-biphenyl)-4-yl]-3,4-dihydroxy-5-methyl-2(5H)-furanone starting with ethyl 4-isobutylbenzoylformate. (R)-(−)-Phenylglycinol was used to resolve the methyl (R)-(−)-2-(4-isobutylphenyl)propionate enantiomer, of which 1.2 g, (5 mmol) was converted into 190 mg (15% yield) of (R)-(−)-3,4-dihydroxy-5-methyl-5-[4-(2-methylpropyl)phenyl]-2(5H)-furanone as a white crystalline material: mp 180–181° C. dec. (CHCl$_3$/hexanes); [α]$^{25}_D$−137° (c=1.27; MeOH); $^1$H NMR (acetone-d$_6$) δ 7.44–7.14 (m, 4H), 2.48 (d, 2H, J=7.1 Hz), 1.87–1.82 (m, 1H), 1.83 (s, 3H), 0.88 (d, 6H, J=6.5 Hz). Anal Calcd for C$_{15}$H$_{18}$O$_4$: C, 68.68; H, 6.92. Found: C, 68.52; H, 7.01.

EXAMPLE 14

(S)-(+)-3,4-Dihydroxy-5-methyl-5-[4-(2-methylpropyl)phenyl]-2(5H)-furanone (S)-(+)-3,4-Dihydroxy-5-methyl-5-[4-(2-methylpropyl)phenyl]-2(5H)-furanone was synthesized in an analogous manner used for the production of(R)-(−)-5-[(1,1'-biphenyl)-4-yl]-3,4-dihydroxy-5-methyl-2(5H)-furanone starting with ethyl 4-isobutylbenzoylformate. (S)-(+)-Phenylglycinol was used to resolve the methyl (S)-(+)-2-(4-isobutylphenyl)propionate enantiomer, of which 1.2 g (5 mmol) was converted into 250 mg (19% yield) of (S)-(+)-3,4-dihydroxy-5-methyl-5-[4-(2-methylpropyl)phenyl]-2(5H)-furanone as a white crystalline material: mp 175–177° C. dec. (CHCl$_3$/hexanes); [α]$^{25}_D$+132° (c=1.55; MeOH) $^1$H NMR (acetone-d$_6$) δ 7.44–7.14 (m, 4H), 2.48 (d, 2H, J=7.1 Hz), 1.87–1.82 (m, 1H), 1.83 (s, 3H), 0.88 (d, 6H, J=6.5 Hz). Anal Calcd for C$_{15}$H$_{18}$O$_4$: C, 68.68; H, 6.92. Found: C, 68.08; H, 6.90.

EXAMPLE 15

3,4-Dihydroxy-5-[2-(4-phenoxy)phenoxyethyl]-2(5H)-furanone

A. A mixture consisting of 340 mg (1.0 mmol) of 3,4-dibenzyloxy-5-(2-hydroxyethyl)-2(5H)-furanone, 320 mg (1.3 mmol) of triphenylphosphine and 225 mg (1.2 mmol) of 4-phenoxyphenol was dissolved in 8 mL of anhydrous THF under argon. Diisopropyl azodicarboxylate (276 µL 1.4 mmol) was added to the solution dropwise with stirring at 25° C. After 36 hours the reaction mixture was poured into 30 mL of H$_2$O and extracted with two 30 mL portions of ether. The combined ether fractions were washed with 25 mL of saturated NaHCO$_3$ solution, 25 mL of H$_2$O, 25 mL of aqueous 10% HCl solution, 25 mL of H$_2$O, 25 mL of brine, dried (MgSO$_4$) and concentrated to an oil. The product was purified over silica gel using EtOAc/hexanes (2/3) as eluant to provide 3,4-dibenzyloxy-5-[2-(4-phenoxy)phenoxyethyl]-2(5H)-furanone as an oil.

B. The 3,4-dibenzyloxy-5-[2-(4-phenoxy)phenoxyethyl]-2(5H)-furanone was hydrogenated in 50 mL of MeOH over 50 mg of 5% Pd/BaSO$_4$ under 30psi H$_2$. After completion of the reaction, as determined by TLC analysis, the suspension was filtered through celite, washed with three 10 mL portions of MeOH and concentrated to a white solid. Trituration with ether and hexanes provided 150 mg (44% yield) of 3,4-dihydroxy-5-[2-(4-phenoxy)phenoxyethyl]-2(5H)-furanone as a white powder: mp 125–127° C., $^1$H NMR (acetone-d$_6$) δ 7.42–7.28 (m, 2H), 7.12–6.88 (m, 7H), 4.95 (dd, 1H), 4.17 (q$_{ab}$, 2H), 2.55–2.36 (m, 1H), 2.05–1.87 (m, 1H); $^{13}$C NMR (acetone-d$_6$) δ 169.41, 158.91, 155.57, 153.39, 150.61, 129.98, 122.73, 120.94, 117.71, 116.32, 115.99, 72.43, 63.97, 32.43; Anal Calcd for C$_{18}$H$_{16}$O$_6$+0.5 H$_2$O; C, 64.12; H, 5.04: Found C, 64.28; H, 5.04.

EXAMPLE 16

3,4-Dihydroxy-5-[2-(flavone-6-oxy)ethyl]-2(5H)-furanone

Mitsunoble coupling of 0.33 g (1.4 mmol) of 6-hydroxyflavone with 0.40 g (1.17 mmol) of 3,4-dibenzyloxy-5-(2-hydroxyethyl)-2(5H)-furanone and subsequent benzyl group deprotection by hydrogenation were performed in a similar manner as described in the synthesis of 3,4-dihydroxy-5-[2-(4-phenoxy)phenoxyethyl]-2(5H)-furanone to provide 3,4-dihydroxy-5-[2-(flavone-6-oxy)ethyl]-2(5H)-furanone as a tan solid: mp 200–220° C. dec. (acetone/hexanes), $^1$H NMR (DMSO-d$_6$) δ 8.13–7.36 (m, 8H), 7.01 (s, 1H), 4.92 (dd, 1H), 4.17 (t, 2H), 2.47–2.27 (m, 1H), 1.98–1.85 (m, 1H). $^{13}$C NMR (DMSO-d$_6$) δ 177.23, 170.22, 162.71, 156.02, 155.36, 150.80, 132.06, 131.51, 129.42, 126.59, 124.31, 123.85, 120.49, 117.44, 106.43, 105.85, 72.24, 64.20, 31.71. Anal Calcd for C$_{21}$H$_{16}$O$_7$+0.25 H$_2$O: C, 65.55; H, 4.44. Found: C, 65.59; H, 4.49.

EXAMPLE 17

5-[2-(Dibenzofuran-2-oxy)ethyl]-3,4-dihydroxy-2(5H)-furanone

Mitsunoble coupling of 0.22 g (1.2 mmol) of 2-hydroxydibenzofuran with 0.34 g (1.0 mmol) of 3,4-dibenzyloxy-5-(2-hydroxyethyl)-2(5H)-furanone and subsequent benzyl group deprotection by hydrogenation were performed in a similar manner as described in the synthesis of 3,4-dihydroxy-5-[2-(4-phenoxy)phenoxyethyl]-2(5H)-furanone to provide 40 mg (10% yield) of 5-[2-(dibenzofuran-2-oxy)ethyl]-3,4-dihydroxy-2(5H)-furanone a white solid.: mp 191–192° C. (ether/hexanes), $^1$H NMR (acetone-d$_6$) δ 8.23–8.18 (m, 1H), 7.83–7.44 (m, 5H), 7.28–7.23 (m, 1H), 5.12 (dd, J=5.3, 8.7 Hz, 1H), 4.42 (dd, J=2.6, 4.7 Hz, 2H), 2.69–2.59 (m, 1H), 2.21–2.08 (m, 1H). $^{13}$C NMR (acetone-d$_6$) δ 169.68, 157.31, 155.75, 153.70, 151.31, 127.76, 125.05, 124.83, 123.07, 121.34, 118.46, 116.42, 112.39, 111.90, 105.40, 72.72, 64.57, 32.64. Anal Calcd for C$_{18}$H$_{14}$O$_6$+0.25 H$_2$O: C, 65.36; H, 4.57. Found: C, 65.52; H, 4.23.

EXAMPLE 18

3,4-Dihydroxy-5-[2-(1-naphthoxy)ethyl]-2(5H)-furanone

Mitsunoble coupling of 0.17 g (1.2 mmol) of 1-naphthol with 0.34 g (1.0 mmol) of 3,4-dibenzyloxy-5-(2-hydroxyethyl)-2(5H)-furanone and subsequent benzyl group deprotection by hydrogenation were performed in a similar manner as described in the synthesis of 3,4-dihydroxy-5-[2-(4-phenoxy)phenoxyethyl]-2(5H)-furanone to provide 75 mg (26% yield) of 3,4-dihydroxy-5-[2-(1-naphthoxy)ethyl]-2(5H)-furanone as colorless cubes: mp 163–164° C. (ether/hexanes) $^1$H NMR (acetone-d$_6$) δ 8.38–8.25 (m, 1H), 7.92–7.79 (m, 1H), 7.60–7.34 (m, 4H), 7.05–6.93 (m, 1H), 5.11 (dd, J=5.3, 8.7 Hz, 1H), 4.39 (dd, J=2.6, 4.7 Hz, 2H), 2.75–2.52 (m, 1H), 2.25–2.05 (m, 1H). $^{13}$C NMR (acetone-d$_6$) δ 169.62, 154.92, 153.61, 135.13, 127.83, 126.78, 126.50, 125.92, 125.05, 122.41, 120.66, 118.53, 105.28, 72.85, 63.93, 32.58. Anal Calcd for C$_{16}$H$_{14}$O$_5$: C, 67.11; H, 4.89. Found: C, 66.70; H, 4.88.

EXAMPLE 19

3,4-Dihydroxy-5-[2-(1,8-naphthalimide)-N-ethyl]-2(5H)-furanone

Mitsunoble coupling of 0.24 g (1.2 mmol) of 1,8-naphthalimide with 0.34 g (1.0 mmol) of 3,4-dibenzyloxy- 5-(2-hydroxyethyl)-2(5H)-furanone and subsequent benzyl group deprotection by hydrogenation were performed in a similar manner as described in the synthesis of 3,4-dihydroxy-5-[2-(4-phenoxy)phenoxyethyl]-2(5H)-furanone to provide 150 mg (45% yield) of 3,4-dihydroxy-5-[2-(1,8-naphthalimide)-N-ethyl]-2(5H)-furanone as a white powder: mp 235–250° C. dec. (acetone/hexanes), $^1$H NMR (DMSO-$d_6$) δ 8.62–8.35 (m, 4H), 7.92–7.82 (m, 2H), 4.82 (dd, J=5.3, 8.7 Hz, 1H), 4.19 (t, J=4.2 Hz, 2H), 2.32–2.16 (m, 1H), 1.90–1.75 (m, 1H). $^{13}$C NMR (DMSO-$d_6$) δ 170.29, 163.72, 154.91, 134.56, 131.52, 130.96, 127.60, 127.45, 122.29, 117.46, 73.64, 36.03, 30.58. Anal Calcd for $C_{18}H_{13}NO_6$: C, 63.71; H, 3.86; N, 4.12. Found: C, 63.84; H, 3.83; N, 4.00.

EXAMPLE 20

3,4-Dihydroxy-5-[2-(1,8-naphthosultam)-N-ethyl]-2(5H)-furanone

Mitsunoble coupling of 0.28 g (1.3 mmol) of 1,8-naphthosultam with 0.37 g (1.1 mmol) of 3,4-dibenzyloxy-5-(2-hydroxyethyl)-2(5H)-furanone and subsequent benzyl group deprotection by hydrogenation were performed in a similar manner as described in the synthesis of 3,4-dihydroxy-5-[2-(4-phenoxy)phenoxyethyl]-2(5H)-furanone to provide 100 mg (29% yield) of 3,4-dihydroxy-5-[2-(1,8-naphthosultam)-N-ethyl]-2(5H)-furanone as a light yellow powder: mp 85–95° C. dec. (acetone/hexanes), $^1$H NMR (acetone-$d_6$) δ 8.29–7.55 (m, 5H), 7.12–7.01 (m, 1H), 4.97 (dd, J=4.9, 8.7 Hz, 1H), 4.10 (t, J=4.2 Hz, 2H), 2.72–2.50 (m, 1H), 2.18–1.95 (m, 1H). $^{13}$C NMR (acetone-$d_6$) δ 169.28, 152.93, 136.42, 131.65, 131.10, 130.84, 130.00, 128.82, 120.03, 119.10, 118.60, 118.42, 103.71, 73.01, 37.72, 31.45. Anal Calcd for $C_{16}H_{13}NO_6S+1H_2O$: C, 52.60; H, 4.14; N, 3.83. Found: C, 52.62; H, 3.86; N, 3.56.

EXAMPLE 21

3,4-Dihydroxy-5-[2-(diphenylmethane-2-oxy)ethyl]-2(5H)-furanone

Mitsunoble coupling of 0.28 g (1.3 mmol) of 2-hydroxy diphenylmethane with 0.37 g (1.1 mmol) of 3,4-dibenzyloxy-5-(2-hydroxyethyl)-2(5H)-furanone and subsequent benzyl group deprotection by hydrogenation were performed in a similar manner as described in the synthesis of 3,4-dihydroxy-5-[2-(4-phenoxy)phenoxyethyl]-2(5H)-furanone to provide 140 mg (43% yield) of 3,4-dihydroxy-5-[2-(diphenylmethane-2-oxy)ethyl]-2(5H)-furanone as a white powder, which was purified by trituration with ether and hexanes: $^1$H NMR (acetone-$d_6$) δ 7.33–6.82 (m, 9H), 4.78 (dd, J=5.3, 8.7 Hz, 1H), 4.19 (dd, J=2.6, 4.7 Hz, 2H), 3.96 (s, 2H); 2.57–2.36 (m, 1H), 2.10–1.82 (m, 1H). Anal Calcd for $C_{19}H_{18}O_5$: C, 69.9; H, 5.6. Found: C, 69.75; H, 5.52.

EXAMPLE 22

5-[2-((1,1'-Biphenyl)-4-oxy)ethyl]-3,4-dihydroxy-2(5H)-furanone

Mitsunoble coupling of 0.20 g (1.2 mmol) of 4-hydroxy-1,1'-biphenyl with 0.34 g (1.0 mmol) of 3,4-dibenzyloxy-5-(2-hydroxyethyl)-2(5H)-furanone and subsequent benzyl group deprotection by hydrogenation were performed in a similar manner as described in the synthesis of 3,4-dihydroxy-5-[2-(4-phenoxy)phenoxyethyl]-2(5H)-furanone to provide 100 mg (32% yield) of 5-[2-((1,1'-biphenyl)-4-oxy)ethyl]-3,4-dihydroxy-2(5H)-furanone as a white powder after trituration with ether and hexanes: $^1$H NMR (acetone-$d_6$) δ 7.71–7.02 (m, 9H), 4.97 (dd, J=4.9, 8.7 Hz, 1H), 4.25 (dd, J=2.6, 4.7 Hz, 2H), 2.58–2.41 (m, 1H), 2.10–1.92 (m, 1H). Anal Calcd for $C_{18}H_{16}O_5+1H_2O$: C, 67.49; H, 5.66. Found: C, 67.34; H, 5.42.

EXAMPLE 23

3,4-Dihydroxy-5-[2-(quinoline-2-oxy)ethyl]-2(5H)-furanone

Mitsunoble coupling of 0.17 g (1.2 mmol) of 2-hydroxyquinoline with 0.34 g (1.0 mmol) of 3,4-dibenzyloxy-5-(2-hydroxyethyl)-2(5H)-furanone and subsequent benzyl group deprotection by hydrogenation were performed in a similar manner as described in the synthesis of 3,4-dihydroxy-5-[2-(4-phenoxy)phenoxyethyl]-2(5H)-furanone to provide 50 mg (17% yield) of 3,4-dihydroxy-5-[2-(quinoline-2-oxy)ethyl]-2(5H)-furanone as a fluffy white solid after recrystallization from ether and hexanes: $^1$H NMR (acetone-$d_6$) δ 8.25–8.17 (m, 1H); 7.88–7.38 (m, 4H), 7.01–6.93 (m, 1H); 4.97 (dd, J=4.9, 8.7 Hz, 1H), 4.81–4.55 (m, 2H); 2.62–2.45 (m, 1H), 2.20–1.95 (m, 1H). Anal Calcd for $C_{15}H_{13}NO_5+0.5\ H_2O$: C, 60.81; H, 5.10; N, 4.72. Found: C, 61.04; H, 5.04; N, 4.32.

EXAMPLE 24

3,4-Dihydroxy-5-[2-(4,5-diphenyl-1,3-isoxazole-2-thio)ethyl]-2(5H)-furanone

A suspension of 3.14 g (12.4 mmol) 4,5-diphenyl-2-thio-1,3-isoxazole in 12 mL of THF under argon with stirring at −78° C. was treated with 4.9 mL (12.2 mmol) of 2.5 M nBuLi. The reaction mixture was warmed to −5° C. and 1.1 g (4 mmol) of 3,4-dihydroxy-5-(2-iodoethyl)-2(5H)-furanone dissolved in 12 mL of HMPA was added at a rate to maintain the reaction temperature below 0° C. Stirring continued at 0 to −5° C. for 60 minutes followed by the addition of 100 mL of saturated $NH_4Cl$ solution. The mixture was extracted with 2×100 mL portions of ether/EtOAc (1/1). The organic fractions were combined and extracted with 3×50 mL of saturated $NaHCO_3$ solution. The bicarbonate extracts were combined, washed with 2×50 mL of ether, acidified to pH 1 with 10% HCl solution and extracted into 2×100 mL portions of ether. The ether extracts were combined and washed successively with 40 mL of $H_2O$, 40 mL of brine, dried ($MgSO_4$) and concentrated to an oil.

Purification over $SiO_2$ using acetone/hexanes (1:1 to 2:3 to 7:3) provided a brown colored solid upon evaporation of solvent. The solid was taken up in 100 mL of ether and extracted with 3×50 mL of $NaHCO_3$ solution. The combined aqueous extracts were acidified with 10% HCl solution and extracted with 2×100 mL portions of ether. The organic portions were washed with 40 mL of $H_2O$, 40 mL of brine, dried ($MgSO_4$) and concentrated to provide 875 mg (55% yield) of 3,4-dihydroxy-5-[2-(4,5-diphenyl-1,3-isoxazole-2-thio)ethyl]-2(5H)-furanone as a white foam: mp 88–91° C., $^1$H NMR (acetone-$d_6$) δ 7.67–7.39 (m, 10 H), 4.95 (dd, J=3.7, 8.7 Hz, 1H), 3.61–3.28 (m, 2H), 2.72–2.19 (m, 2H). $^{13}$C NMR (acetone-$d_6$) δ 169.17, 159.13, 152.70, 147.65, 136.83, 132.60, 129.14 (2C), 128.85 (2C), 128.61, 128.11, 126.92, 118.91, 74.25, 32.69, 27.32. Anal Calcd for $C_{21}H_{17}NO_5S+0.25\ H_2O$: C, 63.07; H, 4.41; N, 3.50. Found: C, 63.23; H, 4.70; N, 3.24.

EXAMPLE 25

3,4-Dihydroxy-5-[2-(naphthyl-1-thio)ethyl]-2(5H)-furanone

1-Naphthalenethiol (430 μL, 3.1 mmol) and 0.27 g (1 mmol) of 3,4-dihydroxy-5-(2-iodoethyl)-2(5H)-furanone were reacted in an analogous manner as described for the synthesis of 3,4-dihydroxy-5-[2-(4,5-diphenyl-1,3-isoxazole-2-thio)ethyl]-2(5H)-furanone to provide 90 mg (30% yield) of 3,4-dihydroxy-5-[2-(naphthyl-1-thio)ethyl]-2(5H)-furanone as a colorless oil. Additional purification by chromatography over $SiO_2$ was not necessary for this compound: $^1$H NMR (acetone-$d_6$) δ 8.44–8.32 (m, 1H), 7.98–7.43 (m, 6H), 4.92 (dd, J=3.7, 8.7 Hz, 1H), 3.28–3.06 (m, 2H), 2.39–2.19 (m, 1H), 2.02–1.84 (m, 1H). Anal Calcd for $C_{16}H_{14}O_4S+0.25 H_2O$: C, 62.63; H, 4.76. Found: C, 63.06; H, 5.19.

EXAMPLE 26

3,4-Dihydroxy-5-[2-(naphthyl-2-thio)ethyl]-2(5H)-furanone

2-Naphthalenethiol (430 μL, 3.1 mmol) and 0.27 g (1 mmol) of 3,4-dihydroxy-5-(2-iodoethyl)-2(5H)-furanone were reacted in an analogous manner as described for the synthesis of 3,4-dihydroxy-5-[2-(4,5-diphenyl-1,3-isoxazole-2-thio)ethyl]-2(5H)-furanone to provide 140 mg (46% yield) of 3,4-dihydroxy-5-[2-(naphthyl-2-thio)ethyl]-2(5H)-furanone as a white powder after trituration with ether and hexanes. Additional purification by chromatography over $SiO_2$ was not necessary for this compound: $^1$H NMR (acetone-$d_6$) δ 7.95–7.82 (m, 4H), 7.58–7.40 (m, 3H), 4.92 (dd, J=3.7, 8.7 Hz, 1H), 3.34–3.08 (m, 2H), 2.42–2.21 (m, 1H), 2.02–1.86 (m, 1H). $^{13}$C NMR (acetone-$d_6$) δ 169.53, 153.03, 134.48, 134.09, 132.29, 128.99, 128.13, 127.49, 127.41, 127.08, 126.65, 126.14, 118.68, 74.25, 32.33, 27.81. Anal Calcd for $C_{16}H_{14}O_4S$: C, 63.56; H, 4.67. Found: C, 63.44; H, 4.58.

EXAMPLE 27

3,4-Dihydroxy-5-[(4-phenyl)-3-butynyl]-2(5H)-furanone

To a flame dried reaction flask fitted with an argon inlet, septum and magnetic stir bar, were added 58 mg (0.05 mmol) of Pd(PPh$_3$)$_4$, 225 μL (2.0 mmol) of iodobenzene, 0.17 g (1.0 mmol) of 5-(3-butynyl)-3,4-dihydroxy-2(5H)-furanone, 2 mL of pyrrolidine and 20 mg (0.10 mmol) of copper (I) iodide. The flask was protected from light (foil) and the yellow mixture was stirred at room temperature until the starting 5-(3-butynyl)-3,4-dihydroxy-2(5H)-furanone was not visible by TLC analysis (CHCl$_3$:MeOH 9:1). The reaction mixture was poured into a mixture of 50 g of ice and 10 mL of 37% HCl, and extracted with 2×50 mL of ether. The ether extracts were combined and washed with 2×20 mL of 10% aqueous HCl solution, 20 mL of H$_2$O, 20 mL of brine, dried (MgSO$_4$) and concentrated.

The residue was dissolved in 30 mL of ether and extracted with 3×15 mL of saturated NaHCO$_3$ solution. The bicarbonate extracts were pooled and washed with 10 mL of ether, acidified to pH 2 with 10% HCl solution and extracted with 2×25 mL of ether.

The ether extracts were combined and washed with 10 mL of H$_2$O, 3 mL of 10% (w/w) NaHCO$_3$ solution, 10 mL of H$_2$O, 10 mL of brine, dried (MgSO$_4$) and concentrated to provide 3,4-dihydroxy-5-[(4-phenyl)-3-butynyl]-2(5H)-furanone as a white solid: mp 145–146° C.; $^1$H NMR (acetone-$d_6$) δ 7.35–7.15 (m, 5H) 4.75 (dd, J=3.4, 8.2 Hz, 1H), 2.50–2.40 (m, 2H), 2.20–2.05 (m, 1H), 1.75–1.60 (m, 1H); $^{13}$C NMR (acetone-$d_6$) δ 170.2, 153.8, 132.3, 129.2, 128.7, 124.6, 119.0, 89.3, 82.1, 74.9, 32.4, 15.3.

EXAMPLE 28

3,4-Dihydroxy-5-[(4-(2-methyl)phenyl)-3-butynyl]-2(5H)-furanone 5-(3-Butynyl)-3,4-dihydroxy-2(5H)-furanone (0.17 g, 1.0 mmol) and 256 μL (2.0 mmol) of 2-iodotoluene were coupled in an analogous fashion as described for the synthesis of 3,4-dihydroxy-5-[(4-phenyl)-3-butynyl]-2(5H)-furanone. The residue was purified over silica gel using CHCl$_3$/MeOH (96/4) as eluant to provide 3,4-dihydroxy-5-[(4-(2-methyl)phenyl)-3-butynyl]-2(5H)-furanone as a light yellow solid: mp 111–112° C., $^1$H NMR (CDCl$_3$) δ 7.37–7.07 (m, 4H), 5.01 (dd, J=3.5, 8.5 Hz, 1H), 2.69–2.65 (m, 2H), 2.40 (s, 3H), 2.39–2.27 (m, 1H), 1.97–1.86 (m, 1H); $^{13}$C NMR (CDCl$_3$) δ 173.6, 155.8, 140.0, 131.9, 129.3, 127.9, 125.5, 123.1, 117.5, 91.5, 80.9, 76.4, 31.3, 20.7, 15.3; Anal Calcd for $C_{15}H_{14}O_4$: C, 69.76; H, 5.46. Found: C, 69.41; H, 5.58.

EXAMPLE 29

3,4-Dihydroxy-5-[(4-(2-(2Z-hexenyl))phenyl)-3-butynyl]-2(5H)-furanone 5-(3-Butynyl)-3,4-dihydroxy-2(5H)-furanone (0.34 g, 2.0 mmol) and 1.1 g (4.0 mmol) of 2-(2Z-hexenyl)iodobenzene were coupled in an analogous fashion as described for the synthesis of 3,4-dihydroxy-5-[(4-phenyl)-3-butynyl]-2(5H)-furanone. The residue was purified over silica gel using CHCl$_3$/MeOH (96/4) as eluant and dried at 0.05 mm Hg at 58° C. for 2 h to provide 100 mg (17% yield) of 3,4-dihydroxy-5-[(4-(2-(2Z hexenyl))phenyl)-3-butynyl]-2 (5H)-furanone as a yellow oil: $^1$H NMR (acetone-$d_6$) δ 7.43–7.15 (m, 4H), 5.70–5.45 (m, 2H), 4.91 (dd, 1H, J=3.4, 8.3 Hz), 3.57 (d, 2H, J=5.9 Hz), 2.66 (t, 2H, J=7.0 Hz), 2.37–2.11 (m, 3H), 2.00–1.85 (m, 1H), 1.48–1.29 (m, 2H), 0.93 (t, 3H, J=7.3 Hz); Anal Calcd for $C_{20}H_{22}O_4+0.2 H_2O$: C, 72.80; H, 6.84. Found: C, 72.99; H, 6.96.

EXAMPLE 30

3,4-Dihydroxy-5-[(4-(2-(phenylthio)methyl)phenyl)-3-butynyl]-2(5H)-furanone 5-(3-Butynyl)-3,4-dihydroxy-2(5H)-furanone (0.12 g, 0.71 mmol) and 0.35 g (1.1 mmol) of 2-(phenylthio)methyl-1-iodobenzene were coupled in an analogous fashion as described for the synthesis of 3,4-dihydroxy-5-[(4-phenyl)-3-butynyl]-2(5H)-furanone. The residue was purified over silica gel using CHCl$_3$/MeOH/AcOH (96/3/1) as eluant and dried at 0.05 mm Hg at 58° C. for 2 h to provide 180 mg (69%) of 3,4-dihydroxy-5-[(4-(2-(phenylthio)methyl) phenyl)-3-butynyl]-2(5H)-furanone a light yellow oil: $^1$H NMR (acetone-$d_6$) δ 7.44–7.19 (m, 9H), 4.90 (dd, J=3.3, 8.3 Hz, 1H), 4.36 (s, 2H), 2.63 (t, J=7.6 Hz, 2H), 2.28–2.21 (m, 1H), 1.90–1.81 (m, 1H); Anal Calcd for $C_{21}H_{18}O_4S$: C, 68.85; H, 4.95. Found: C, 68.63; H, 5.11.

EXAMPLE 31

3,4-Dihydroxy-5-[(4-(2-phenylsulfonamide-(N-butyl))-3-butynyl]-2(5H)-furanone 5-(3-Butynyl)-3,4-dihydroxy-2(5H)-furanone (0.17 g, 1.0 mmol) and 400 mg (1.2 mmol) of N-butyl-2-iodobenzenesulfonamide were coupled in an analogous fashion as described for the synthesis of 3,4-dihydroxy-5-[(4-phenyl)-3-butynyl]-2(5H)-furanone. The residue was purified over silica gel using CHCl$_3$/MeOH/AcOH (500/16/0.5) as eluant and dried at 0.05 mm Hg at 58° C. for 2 h to provide 3,4-dihydroxy-5-[(4-(2-phenylsulfonamide-(N-butyl))-3-butynyl]-2(5H)-furanone as a light yellow oil: $^1$H NMR (acetone-$d_6$) δ 8.00–7.96 (m, 1H), 7.59–7.55 (m, 1H), 7.33–7.24 (m, 2H), 6.66 (s, 1H), 4.82 (dd, J=3.4, 8.3 Hz, 1H), 3.44–3.36 (m, 2H), 3.23–3.14 (m, 2H), 2.52–2.45 (m, 1H), 2.00–1.94 (m, 1H), 1.69–1.53 (m, 2H), 1.43–1.29 (m, 2H), 0.81 (t, J=7.2 Hz, 3H); $^{13}$C NMR (acetone-$d_6$) δ 169.8, 153.5, 141.6, 137.6, 130.0, 124.2, 123.8, 120.9, 118.6, 114.4, 108.7, 74.8, 53.6, 32.0, 24.9, 24.1, 20.9, 12.9; Anal Calcd for $C_{18}H_{21}NO_6S$: C, 56.99; H, 5.58; N, 3.69. Found: C, 56.71; H, 5.65; N, 3.48.

EXAMPLE 32

3,4-Dihydroxy-5-[4-(2-naphthyl)-3-butynyl]-2(5H)-furanone 5-(3-Butynyl)-3,4-dihydroxy-2(5H)-furanone (0.17 g, 1.0 mmol) and 300 μL (2.0 mmol) of 2-iodonaphthalene were coupled in an analogous fashion as described for the synthesis of 3,4-dihydroxy-5-[(4-phenyl)-3-butynyl]-2(5H)-furanone. The residue was purified over silica gel using $CHCl_3$/MeOH/AcOH (96/3/1) as eluant and dried at 0.05 mm Hg at 58° C. for 2 h to provide 230 mg (75%) of 3,4-dihydroxy-5-[4-(2-naphthyl)-3-butynyl]-2(5H)-furanone as a yellow wax: $^1$H NMR (acetone-$d_6$) δ 8.4–8.3 (m, 1H), 7.96–7.88 (m, 2H), 7.70–7.43 (m, 4H), 4.98 (dd, J=3.4, 8.3 Hz, 1H), 2.82–2.75 (m, 2H), 2.48–2.29 (m, 1H), 2.00–1.85 (m, 1H); Anal Calcd for $C_{18}H_{14}O_4$+0.5 $H_2O$: C, 71.27; H, 4.98. Found: C, 71.33; H, 4.87.

EXAMPLE 33

3,4-Dihydroxy-5-[(4-(2-(propylthio)methyl)phenyl)-3-butynyl]-2(5H)-furanone 5-(3-Butynyl)-3,4-dihydroxy-2(5H)-furanone (0.17 g, 1.0 mmol) and 440 mg (1.5 mmol) of 2-(propylthio)methyl]-iodobenzene were coupled in an analogous fashion as described for the synthesis of 3,4-dihydroxy-5-[(4-phenyl)-3-butynyl]-2(5H)-furanone. The residue was purified over silica gel using $CHCl_3$/MeOH/AcOH (500/16/0.5) as eluant and dried at 0.05 mm Hg at 58° C. for 2 h to provide 240 mg (72% yield) of 3,4-dihydroxy-5-[(4-(2-(propylthio)methyl)phenyl)-3-butynyl]-2(5H)-furanone as a yellow oil: $^1$H NMR (acetone-$d_6$) δ 7.44–7.21 (m, 4H), 4.90 (dd, J=3.4, 8.3 Hz, 1H), 3.89 (s, 2H), 2.70–2.63 (m, 2H), 2.48–2.41 (m, 2H), 2.26–2.21 (m, 1H), 1.90–1.81 (m, 1H) 1.64–1.53 (m, 2H), 0.93 (t J=7.3 Hz, 3H); Anal Calcd for $C_{18}H_{20}O_4S$: C, 65.05; H, 6.07. Found: C, 64.51; H, 6.28.

EXAMPLE 34

3,4-Dihydroxy-5-[(4-(2-(1-pentylthio)methyl)phenyl)-3-butynyl]-2(5H)-furanone 5-(3-Butynyl)-3,4-dihydroxy-2(5H)-furanone (84 mg, 0.5 mmol) and 240 mg (0.75 mmol) of 2-(methyl-1-pentylsulfide)iodobenzene were coupled in an analogous fashion as described for the synthesis of 3,4-dihydroxy-5-[(4-phenyl)-3-butynyl]-2(5H)-furanone. The residue was purified over silica gel using $CHCl_3$/MeOH/AcOH (500/16/0.5) as eluant and dried at 0.05 mm Hg at 58° C. for 2 hours to provide 3,4-dihydroxy-5-[(4-(2-(pentylthio)methyl)phenyl)-3-butynyl]-2(5H)-furanone: $^1$H NMR (acetone-$d_6$) δ 7.43–7.21 (m, 4H), 4.95 (dd, J=3.4, 8.4 Hz, 1H), 3.89 (s, 2H), 2.70–2.63 (m, 2H), 2.50–2.43 (m, 2H), 2.26–2.21 (m, 1H), 2.00–1.81 (m, 1H) 1.66–1.45 (m, 2H), 1.43–1.20 (m, 4H), 0.87 (t, J=7.2 Hz, 3H); Anal Calcd for $C_{20}H_{24}O_4S$+0.5 $H_2O$: C, 65.02; H, 6.82. Found: C, 65.38; H, 6.69.

EXAMPLE 35

3,4-Dihydroxy-5-[(4-(2-(propylsulfonyl)methyl)phenyl)-3-butynyl]-2(5H)-furanone 5-(3-Butynyl)-3,4-dihydroxy-2(5H)-furanone (236 mg, 1.2 mmol) and 600 mg (1.5 mmol) of 2-methyl-(1-propylsulfone)iodobenzene were coupled in an analogous fashion as described for the synthesis of 3,4-dihydroxy-5-[(4-phenyl)-3-butynyl]-2(5H)-furanone. The residue was purified over silica gel using $CHCl_3$/MeOH/AcOH (500/16/0.5) as eluant and dried at 0.05 mm Hg at 58° C. for 2 h to provide 250 mg (50% yield) of 3,4-dihydroxy-5-[(4-(2-(propylsulfonyl)methyl)phenyl)-3-butynyl]-2(5H)-furanone as a light yellow oil: $^1$H NMR (acetone-$d_6$) δ 7.56–7.34 (m, 4H), 4.96 (dd, J=3.4, 8.2 Hz, 1H), 4.57 (s, 2H), 3.03–2.95 (m, 2H), 2.71–2.64 (m, 2H), 2.35–2.26 (m, 1H), 1.94–1.70 (m, 3H), 1.02 (t, J=7.4 Hz, 3H); $^{13}$C NMR (acetone-$d_6$) δ 169.9, 153.5, 132.9, 132.1, 131.0, 128.9, 128.5, 125.3, 118.6, 94.0, 79.6, 74.4, 57.2, 54.0, 31.5, 15.7, 14.8, 12.7; Anal Calcd for $C_{18}H_{20}O_6S$: C, 59.34; H, 5.53. Found: C, 58.93; H, 5.76.

EXAMPLE 36

3,4-Dihydroxy-5-[2-(4-(4-fluorophenylmethyl)thiophene)-(3-butynyl)]-2(5H)-furanone 5-(3-Butynyl)-3,4-dihydroxy-2(5H)-furanone (750 mg, 4.5 mmol) and 2.6 g (8.2 mmol) of 4-(4-fluorophenylmethyl)-2-iodothiophene were coupled in an analogous fashion as described for the synthesis of 3,4-dihydroxy-5-[(4-phenyl)-3-butynyl]-2(5H)-furanone. The residue was purified over silica gel using $CHCl_3$/MeOH/AcOH (500/15/0.5) as eluant and dried at 0.05 mm Hg at 58° C. for 2 h to provide 1.2 g (75% yield) of 3,4-dihydroxy-5-[2-(4-(4-fluorophenylmethyl)thiophene)-(3-butynyl)]-2(5H)-furanone as a brown wax: mp 119–121° C. $^1$H NMR (acetone-$d_6$) δ 7.38–7.25 (m, 2H), 7.13–6.99 (m, 3H), 6.78–6.74 (m, 1H), 4.84 (dd, J=3.3, 8.1 Hz, 1H), 4.14 (s, 2H), 2.59 (t, J=7.1 Hz, 2H), 2.38–2.14 (m, 1H), 1.90–1.69 (m, 1H); $^{13}$C NMR (acetone-$d_6$) δ 169.19, 164.04 157.29, 152.78, 145.79, 136.74, 131.80, 130.80, 130.47, 125.54, 122.74, 118.84, 115.89, 115.03, 92.44, 74.90, 74.31, 35.14, 31.84, 15.02; Anal Calcd for $C_{19}H_{15}FO_4S$: C, 63.69; H, 4.22. Found: C, 63.42; H, 4.33.

EXAMPLE 37

3,4-Dihydroxy-5-(4-phenylbutanyl)-2(5H)-furanone

Quinoline (70 μL, 0.6 mmol), 15 mg of 5% Pd/$BaSO_4$ and 61 mg (0.25 mmol) of 3,4-dihydroxy-5-[(4-phenyl)-3-butynyl]-2(5H)-furanone were combined in 20 mL of ethanol and hydrogenated at atmospheric pressure until 12 mL (0.5 mmol) of $H_2$ was consumed as measured by a $H_2O$ filled burette. The catalyst was removed by filtration through two #1 fluted filter papers and the solution was concentrated to a volume of about 5 mL, taken up in 50 mL of ether and washed with 3×15 mL of 5% aqueous HCl, 20 mL of $H_2O$ and 20 mL of brine, dried ($MgSO_4$) and concentrated to provide 3,4-dihydroxy-5-(4-phenylbutanyl)-2(5H)-furanone as a brown wax: $^1$H NMR (acetone-$d_6$) δ 7.28–7.13 (m, 5H), 4.66 (dd, J=3.4, 7.2 Hz, 1H), 2.62 (t, J=7.7, 2H), 2.00–1.93 (m, 1H), 1.69–1.42 (m, 5H); $^{13}$C NMR (acetone-$d_6$) δ 170.7, 154.9, 143.3, 129.2, 129.1, 126.5, 118.6, 76.2, 36.3, 32.7, 32.1, 24.6. Anal Calcd for $C_{14}H_{16}O_4$+0.25 $H_2O$: C, 66.52; H, 6.58. Found: C, 66.71; H, 6.75.

EXAMPLE 38

3,4-Dihydroxy-5-[(4-phenyl)-3Z-butenyl]-2(5H)-furanone

Quinoline (70 μL, 0.6 mmol), 15 mg of 5% Pd/$BaSO_4$ and 62 mg (0.25 mmol) of 3,4-dihydroxy-5-[(4-phenyl)-3- butynyl]-2(5H)-furanone were combined in 20 mL of ethanol and hydrogenated at atmospheric pressure until 6 mL (0.25 mmol) of $H_2$ was consumed as measured by a $H_2O$ filled burette. The catalyst was removed by filtration through 2 fluted filter papers and the solution was concentrated, taken up in 50 mL of ether and washed with 3×15 mL of 5% aqueous HCl, 20 mL of $H_2O$ and 20 mL of brine, dried ($MgSO_4$) and concentrated to give 3,4-dihydroxy-5-[(4-phenyl)-3Z-butenyl]-2(5H)-furanone as the major constituent in a mixture of alkyne, cis alkene and alkane (1.0/5.0/0.5) as determined by $^1H$ NMR spectra: $^1H$ NMR ($CDCl_3$) δ 7.34–7.14 (m, 5H), 6.46 (d, J=11.5 Hz, 1H), 5.65–5.57 (m, 1H), 4.77 (dd, 3.5, 8.0 Hz, 1H), 2.49 (dd, $J_{ab}$=7.6 Hz, 2H), 2.16–2.09 (m, 1H), 1.80–1.70 (m, 1H); $^{13}C$ NMR ($CDCl_3$) δ 173.4, 155.9, 137.1, 130.4, 130.3, 128.7, 128.3, 128.3, 126.8, 117.5, 77.2, 31.8, 23.5.

EXAMPLE 39

3,4-Dihydroxy-5[(4-(2-methyl)phenyl)-3Z-butenyl]-2(5H)-furanone 3,4-Dihydroxy-5[(4-(2-methyl)phenyl)-3-butynyl]-2(5H)- furanone (65 mg, 0.25 mmol) was reduced in a similar manner as described for the synthesis of 3,4-dihydroxy-5-[(4-phenyl)-3Z-butenyl]-2(5 h)-furanone to produce 3,4-dihydroxy-5[(4-(2-methyl)phenyl)-3Z-butenyl]-2(5 h)-furanone as an oil consisting of only the cis isomer as observed by the $^1H$ NMR spectra. $^1H$ NMR ($CDCl_3$) δ 7.34–7.20 (m, 4H), 6.59 (d, J=1 1.4 Hz, 1H), 5.81–5.73 (m, 1H), 4.81 (dd, J=3.4, 8.2 Hz, 1H), 2.49–2.35 (m, 2H), 2.33 (s, 3H), 2.17–2.13 (m, 1H), 1.81–1.75 (m, 1H); $^{13}C$ NMR ($CDCl_3$) δ 173.6, 136.2, 136.2, 130.2, 129.9, 129.6, 128.8, 127.1, 125.5, 117.4, 77.3, 31.9, 23.4, 19.9.

EXAMPLE 40

3,4-Dihydroxy-5[(4-(2-(2Z-hexenyl))phenyl)-3Z-butenyl]-2(5H)-furanone 3,4-Dihydroxy-5[(4-(2-(2-hexynyl))phenyl)-3Z-butenyl]-2(5H)-furanone (75 mg, 0.25 mmol) was reduced in a similar manner as described for the synthesis of 3,4-dihydroxy-5-[(4-phenyl)-3Z-butenyl]-2(5H)-furanone to produce 3,4-dihydroxy-5[(4-(2-(2Z-hexenyl))phenyl)-3Z-butenyl]-2(5H)-furanone as an oil consisting of only the cis isomer as observed by the $^1H$ NMR spectra and contaminated with less than 5% of starting material, which was not separable from the product: $^1H$ NMR (acetone-$d_6$) δ 7.25–7.15 (m, 4H), 6.59 (d, 1H, J=11.4 Hz), 5.81–5.76 (m, 1H), 5.51–5.43 (m, 2H), 4.71 (dd, 1H, J=3.5, 7.6 Hz), 3.44–3.25 (m, 2H), 2.40–1.90 (m, 5H), 1.76–1.58 (m, 1H), 1.50–1.32 (m, 2H), 0.94 (t, 3H, J=7.3 Hz). Anal Calcd for $C_{20}H_{24}O_4$+0.25 $H_2O$: C, 71.20; H, 7.47. Found: C, 70.97; H, 7.32.

The following is a list of references related to the above disclosure. These references should be considered as incorporated by reference in their entirety.
1. Shimuzu, T., et al. Enzyme with dual lipoxygenase activities catalyzes leukotriene A4 synthetase from arachidonic acid. *Pro. Natl. Acad. Sci.* 81:689–693, (1984).
2. Egan, R W and Gale P H, Inhibition of mammalian 5-lipoxygenase by aromatic disulfides, *J. Biol. Chem.* 260: 11554–11559, (1985).
3. Evans, AT, et al Actions of cannabis constituents on enzymes of arachidonic metabobilism: anti-inflammatory potential. *Biochem Pharm.* 36:2035–2037, (1987).
4. Boopathy, R and Baiasubramanian A S. Purification and characterization of sheep platelet cyclooxygenase. *Biochem J.* 239:371–377, (1968).
5. O'Sullivan, MG et al, Lipopolysaccharide induces prostaglandin H synthase-2 in alveolar macrophages. *Biochem. Biophys. Res. Comm.* 187: 1123–1127, (1992).
6. Mansuy D. et al, A new potent inhibitor of lipid peroxidation in vitro and in vivo, the hepatoprotective drug anisyldithiolthione. *Biochem. Biophys. Res. Comm.* 135:1015–1021, (1986).

What is claimed is:

1. A racemic or optically active compound of the formula Ia

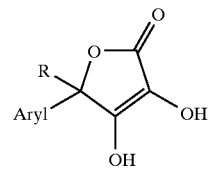

(Ia)

wherein R is phenyl or a lower alkyl; and Aryl is a substituted or unsubstituted aryl group; or a pharmaceutically acceptable salt thereof.

2. A compound according to claim 1 which is racemic 5-[(1,1'-biphenyl)-4-yl]-3,4-dihydroxy-5-phenyl-2(5H)-furanone; racemic 5-[(1,1'-biphenyl)-4-yl]-3,4-dihydroxy-5-methyl-2(5H)-furanone; racemic 3,4-dihydroxy-5-methyl-5-[4-(2-methylpropyl)phenyl]-2(5H)-furanone; (S)-(+)-5-[(1,1'-biphenyl)-4-yl]-3,4-dihydroxy-5-methyl-2(5H)-furanone; (R)-(−)-5-[(1,1'-biphenyl)-4-yl]-3,4-dihydroxy-5-methyl-2(5H)-furanone; (S)-(+)-3,4-dihydroxy-5-methyl-5-[4-(2-methylpropyl)phenyl]-2(5H)-furanone; or (R)-(−)-3,4-dihydroxy-5-methyl-5-[4-(2-methylpropyl)phenyl]-2(5H)-furanone.

3. A pharmaceutical composition comprising an effective amount of a racemic or optically active compound of the general formula Ia:

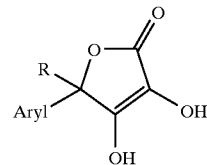

(Ia)

wherein R is phenyl or a lower alkyl; and Aryl is a substituted or unsubstituted aryl group; or a pharmaceutically acceptable salt thereof; together with a pharmaceutically acceptable carrier therefor.

4. A composition according to claim 3 which is racemic 5-[(1,1'-biphenyl)-4-yl]-3,4-dihydroxy-5-phenyl-2(5H)-furanone; racemic 5-[(1,1'-biphenyl)-4-yl]-3,4-dihydroxy-5-methyl-2(5H)-furanone; racemic 3,4-dihydroxy-5-methyl-5-[4-(2-methylpropyl)phenyl]-2(5H)-furanone; (S)-(+)-5-[(1,1'-biphenyl)-4-yl]-3,4-dihydroxy-5-methyl-2(5H)-furanone; (R)-(−)-5-[(1,1'-biphenyl)-4-yl]-3,4-dihydroxy-5-methyl-2(5H)-furanone; (S)-(+)-3,4-dihydroxy-5-methyl-5-[4-(2-methylpropyl)phenyl]-2(5H)-furanone; or (R)-(−)-3,4-dihydroxy-5-methyl-5-[4-(2-methylpropyl)phenyl]-2(5H)-furanone.

5. A method of treating a pathology in which reactive oxygen species and inflammatory mediators are contributing deleterious factors which comprises administration to a patient in need of such therapy an effective amount of a racemic or optically active compound of the formula Ia

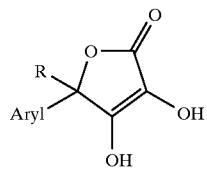
(Ia)

wherein R is phenyl or a lower alkyl; and Aryl is a substituted or unsubstituted aryl group; or a pharmaceutically acceptable salt thereof.

6. A method according to claim 5 which is racemic 5-[(1,1'-biphenyl)-4-yl]-3,4-dihydroxy-5-phenyl-2(5H)-furanone; racemic 5-[(1,1'-biphenyl)-4-yl]-3,4-dihydroxy-5-methyl-2(5H)-furanone; racemic 3,4-dihydroxy-5-methyl-5-[4-(2-methylpropyl)phenyl]-2(5H)-furanone; (S)-(+)-5-[(1,1'-biphenyl)-4-yl]-3,4-dihydroxy-5-methyl-2(5H)-furanone; (R)-(−)-5-[(1,1'-biphenyl)-4-yl]-3,4-dihydroxy-5-methyl-2(5H)-furanone; (S)-(+)-3,4-dihydroxy-5-methyl-5-[4-(2-methylpropyl)phenyl]-2(5H)-furanone; or (R)-(−)-3,4-dihydroxy-5-methyl-5-[4-(2-methylpropyl)phenyl]-2(5H)-furanone.

7. The method of claim 5 wherein said pathology comprises acute or chronic inflammatory disorders.

8. The method of claim 7 wherein said acute or chronic inflammatory disorder is asthma, rheumatoid arthritis, inflammatory bowel disease, or acute respiratory distress syndrome.

9. The method of claim 5 wherein said pathology comprises neurodegenerative disorders.

10. The method of claim 9 wherein said neurodegenerative disorder is Alzheimer disease, Parkinson disease, amyotrophic lateral sclerosis, traumatic brain injury or multiple sclerosis.

11. The method of claim 5 wherein said pathology comprises cardiovascular disease.

12. The method of claim 11 wherein said cardiovascular disease is atherosclerosis.

13. The method of claim 5 wherein said pathology comprises a viral disease.

14. The method of claim 13 wherein said viral disease is AIDS.

15. The method of claim 5 wherein said pathology comprises a skin disease.

* * * * *